United States Patent
Eom

(10) Patent No.: US 9,498,506 B2
(45) Date of Patent: Nov. 22, 2016

(54) **PHARMACEUTICAL COMPOSITION FOR PREVENTING OR TREATING THYROID DISEASES, COMPRISING EXTRACT FROM *LONICERA CAERULEA* L. VAR. *EDULIS* FRUITS AS ACTIVE INGREDIENT**

(71) Applicant: H&K BIOSCIENCE CO., LTD., Seoul (KR)

(72) Inventor: Joo Hwan Eom, Gimpo-si (KR)

(73) Assignee: H&K Bioscience Co., Ltd., Seoul (KR)

( * ) Notice: Subject to any disclaimer, the term of this patent is extended or adjusted under 35 U.S.C. 154(b) by 0 days.

(21) Appl. No.: 15/023,955

(22) PCT Filed: Aug. 5, 2014

(86) PCT No.: PCT/KR2014/007211
§ 371 (c)(1),
(2) Date: Mar. 22, 2016

(87) PCT Pub. No.: WO2015/046743
PCT Pub. Date: Apr. 2, 2015

(65) Prior Publication Data
US 2016/0213725 A1    Jul. 28, 2016

(30) Foreign Application Priority Data

Sep. 24, 2013  (KR) .......................... 10-2013-0113450
Feb. 19, 2014  (KR) .......................... 10-2014-0019294

(51) Int. Cl.
| | | |
|---|---|---|
| A61K 36/355 | (2006.01) |
| A61K 9/19 | (2006.01) |
| A61K 9/08 | (2006.01) |
| A61K 9/00 | (2006.01) |
| A61K 47/22 | (2006.01) |
| A61K 47/26 | (2006.01) |
| A61K 9/20 | (2006.01) |
| A61K 9/48 | (2006.01) |

(52) U.S. Cl.
CPC ............ *A61K 36/355* (2013.01); *A23L 33/105* (2016.08); *A61K 9/0019* (2013.01); *A61K 9/0095* (2013.01); *A61K 9/08* (2013.01); *A61K 9/19* (2013.01); *A61K 9/2018* (2013.01); *A61K 9/2059* (2013.01); *A61K 9/4858* (2013.01); *A61K 9/4866* (2013.01); *A61K 47/22* (2013.01); *A61K 47/26* (2013.01); *A23V 2002/00* (2013.01)

(58) Field of Classification Search
None
See application file for complete search history.

(56) References Cited

U.S. PATENT DOCUMENTS

2010/0074975 A1*  3/2010  Eum .................... A61K 36/355
                                                                 424/725

FOREIGN PATENT DOCUMENTS

| JP | 2003-026582 A | 1/2003 |
|---|---|---|
| KR | 10-2007-0008089 A | 1/2007 |
| KR | 10-0699790 B1 | 3/2007 |
| KR | 10-2011-0006060 A | 1/2011 |
| KR | 10-2011-0064212 A | 6/2011 |
| KR | 2011-0073003 A | 6/2011 |

OTHER PUBLICATIONS

International Search report and written opinion of the PCT/KR2014/0072112 mailed Nov. 28, 2014.
International Search report and written opinion of the PCT/KR2014/007211 mailed Nov. 28, 2014.
Koo et al., "Effects of Lonicerae Flos on the 6-n-propyl-2-thiouracil (PTU)-induced Rat Hypothyroidism", *Korean Journal of Oriental Physiology & Pathology*, 2010, vol. 24, No. 4, pp. 630-637.

* cited by examiner

*Primary Examiner* — Susan Hoffman
(74) *Attorney, Agent, or Firm* — Squirre Patton Boggs (US) LLP

(57) ABSTRACT

The present invention relates to a pharmaceutical composition for preventing or treating thyroid diseases and a food composition for improving thyroid function, comprising an extract from *Lonicera caerulea* L. car. *Edulis* fruits as an active ingredient.

The composition of the present invention may be useful for preventing or treating thyroid diseases such as hypothyroidism, hyperthyroidism, thyroid nodule, or thyroditis, and improving thyroid function. Since the extract from *Lonicera caerulea* L. car. *Edulis* fruits, which is an active ingredient of the present invention, is derived from natural products, there is no concern for side effects such as toxicity compared to synthetic medicine.

8 Claims, 11 Drawing Sheets

PHARMACEUTICAL COMPOSITION FOR PREVENTING OR TREATING THYROID DISEASES, COMPRISING EXTRACT FROM *LONICERA CAERULEA* L. VAR. *EDULIS* FRUITS AS ACTIVE INGREDIENT

This application claims priority to, and the benefit of, International PCT Patent Application No. PCT/KR2014/007211, entitled PHARMACEUTICAL COMPOSITION FOR PREVENTING OR TREATING THYROID DISEASES, CONTAINING *LONICERA CAERULEA* L. VAR. *EDULIS* FRUIT EXTRACT AS ACTIVE INGREDIENT, filed Aug. 5, 2014, also KR 10-2014-0019294, filed Feb. 19, 2014, and also KR 10-2013-0113450, filed Sep. 24, 2013. The content of each of these patent applications is herein incorporated by reference in its entirety for all purposes.

TECHNICAL FIELD

The present invention relates to a pharmaceutical composition for preventing or treating thyroid diseases and a food composition for improving thyroid function, comprising an extract from *Lonicera caerulea* L. car. *Edulis* fruits as an active ingredient.

BACKGROUND ART

Thyroid, which belongs to an endocrine system, is situated in the center front of the neck and is attached in front of larynx and trachea as a butterfly shape viewed from the front. There is a lobe in each of left and right side and the lobe is connected by an isthmus. Thyroid produces and secretes thyroid hormone and calcitonin, and among these, thyroid hormone, which is formed by iodine as a base material, plays an important role in maintaining body temperature and balance of body metabolism. As a result of these actions, the thyroid hormone is essential for normal growth and development, and maturation of the nervous system.

Thyroid diseases are mainly classified into hyperthyroidism in which the excessive amount of thyroid hormone is secreted, hypothyroidism in which little amount of thyroid hormone is secreted, and thyroid nodule (tumor) caused by hyperplasia of thyroid cells.

If the thyroid does not function properly, basal metabolism is decreased generally because of reduced metabolic activity in the body, and temperature is decreased, and weight can be easily gained. Further, since energy supply is decreased, fatigue comes easily and ability of intellectual activities is also decreased, and this is called hypothyroidism. In contrast, excessive activity of the thyroid shows symptoms including high basal metabolic rate, high body temperature, weight loss, and irritability, and also causes heart strain, and it is called Graves' disease. The thyroid nodule refers to abnormalities in thyroid shape because of lumps formed in the thyroid, and about 10% of the nodules is diagnosed as malignant tumor (thyroid cancer).

As recent trends show a rapid increase of patients suffering from thyroid diseases, the National Health Insurance Service announced 55% increase from 730,000 patients in 2007 to 1,130,000 patients in 2012 in the last five years. In particular, according to the report material from the National Cancer Center, thyroid cancer is ranked as the most frequently occurred cancer in Koreans in 2010 and as the most frequently occurred female cancer (30%). The incidence of thyroid cancer in 2010 compared to 1999 has increased by almost 10 times in both males and females. Thyroid diseases, which are known to occur largely in females, recently developed a trend in which the incidence in male patients rapidly increases, and the number is predicted to be increasing a lot when including the patients suffering from autoimmune thyroid diseases in spite of no defects in thyroid function.

Drug therapy such as synthetic hormones has been utilized for treating hyperthyroidism and hypothyroidism, and specifically, in the case of hyperthyroidism, surgical operation is restrictively applied when thyroid function is inhibited by radioactive iodine therapy or uncontrolled by drug. For thyroiditis and thyroid nodule, treatment including drug therapy or observing development progress is provided based on symptoms. If diagnosed with malignant tumor (thyroid cancer), surgical removal surgery is primarily operated, and next, anti-cancer treatment including thyroid hormone suppressive therapy and radioactive isotope therapy are utilized in combination, but these methods for treatment have limitations on improving side effects and clinical symptoms.

Currently, as for the invention using the extract, Korean Patent No. 10-0699790 relates to a pharmaceutical composition including the extract from *Lonicera caerulea* L. car. *Edulis* fruits that has effects for preventing and treating liver diseases and discloses the effects for preventing and treating diseases including hepatitis, liver cirrhosis, or fatty liver herein. Further, Korean Patent Laid-open Publication No. 10-2009-0130140 discloses health functional food, which has outstanding effects for relieving hangover symptoms while using *Lonicera caerulea* L. car. *Edulis* fruits, and the method for preparing the health functional food. However, as shown in the present invention, the effects on preventing or treating the thyroid diseases by the extract from *Lonicera caerulea* L. car. *Edulis* fruits are unknown.

DISCLOSURE OF INVENTION

Technical Problem

The present inventors have made extensive efforts to obtain new substances, which have outstanding prevention or treatment activity for thyroid diseases, from natural products in order to overcome side effects of conventional treatment methods for thyroid diseases and limitations on the improvement of clinical symptoms. As a result, they have confirmed that the extract from *Lonicera caerulea* L. car. *Edulis* fruits could relieve symptoms of hypothyroidism, hyperthyroidism, thyroditis or thyroid nodule, thereby completing the present invention.

Technical Solution

It is an object of the present invention to provide a pharmaceutical composition for preventing or treating thyroid diseases, comprising an extract from *Lonicera caerulea* L. car. *Edulis* fruits as an active ingredient.

It is another object of the present invention to provide a food composition for improving thyroid function, comprising the extract from *Lonicera caerulea* L. car. *Edulis* fruits as an active ingredient.

It is still another object of the present invention to provide a method for improving or treating thyroid diseases, comprising administering the extract from *Lonicera caerulea* L. car. *Edulis* fruits to a subject who is suspected to have thyroid diseases.

It is still another object of the present invention to provide use of the extract from *Lonicera caerulea* L. car. *Edulis* fruits for a preparation of medicament for prevention or treatment of thyroid diseases.

It is still another object of the present invention to provide use of the extract from *Lonicera caerulea L. car. Edulis* fruits for a preparation of food for prevention or treatment of thyroid diseases.

Advantageous Effects

The composition of the present invention can be useful for preventing or treating thyroid diseases, such as hypothyroidism, hyperthyroidism, thyroid nodule, or thyroiditis; and for improving thyroid function. Since the extract from *Lonicera caerulea L. car. Edulis* fruits, which is an active ingredient of the present invention, is isolated from natural products, there is no concern for side effects such as toxicity compared to synthetic medicine.

Figure 1:
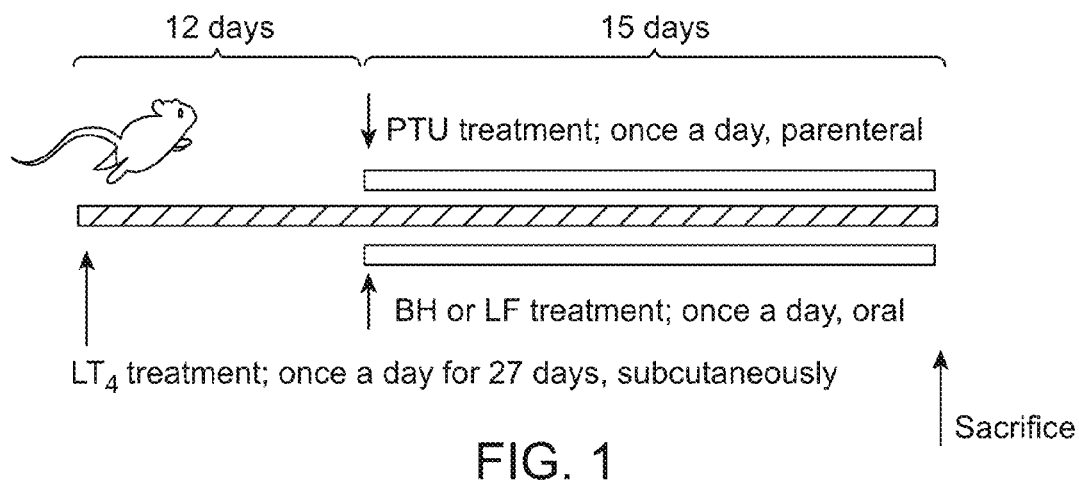
FIG. 1 shows a diagram that shows processes of Example 3 for observing effects on preventing or treating hyperthyroidism by administering the extract from *Lonicera caerulea L. car. Edulis* to a LT4-induced hyperthyroidism animal model.
Figure 2:
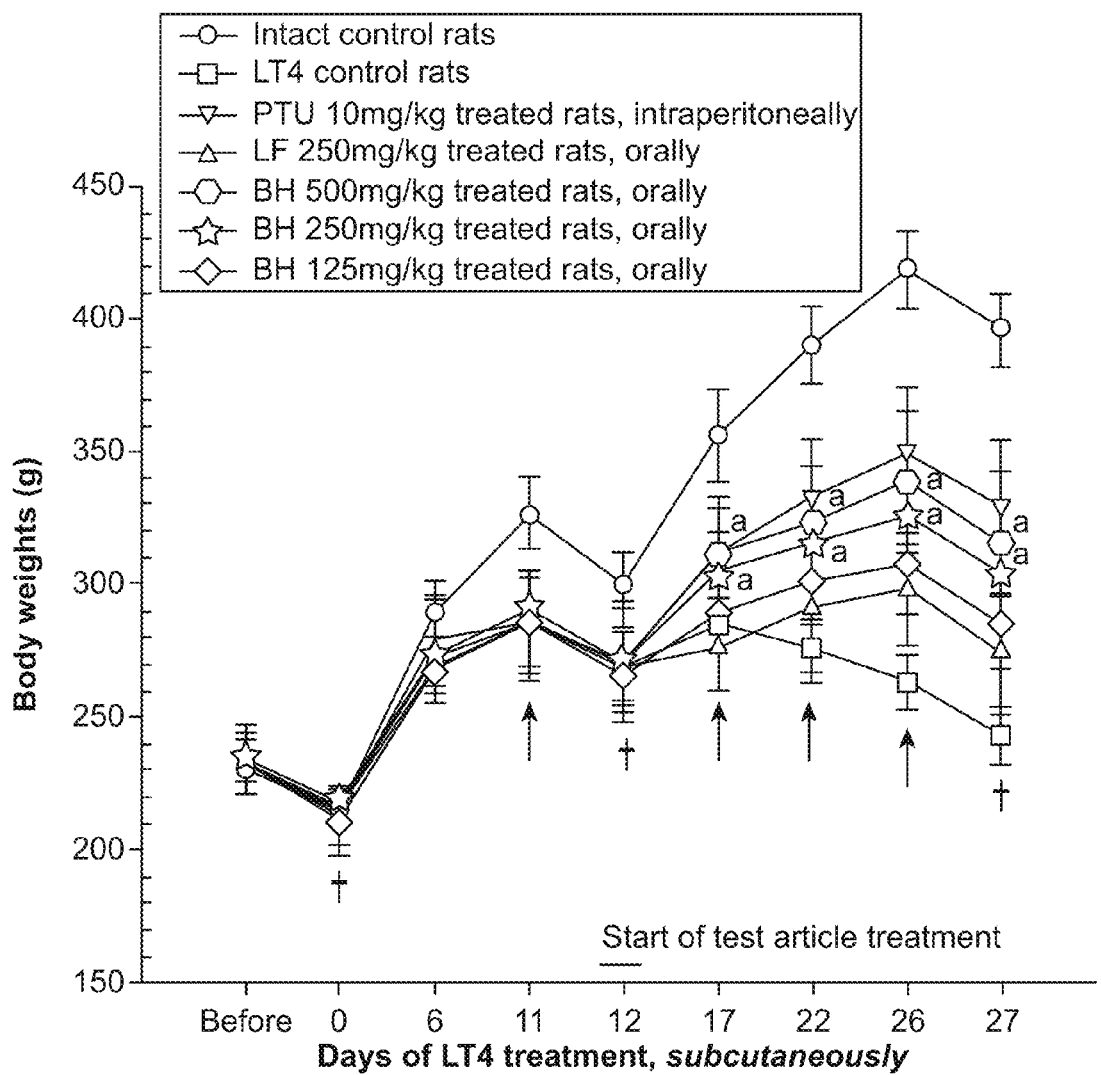
FIG. 2 shows a diagram that shows change in weight for both intact control rat and LT4-induced hyperthyroidism rat.
Figure 3:
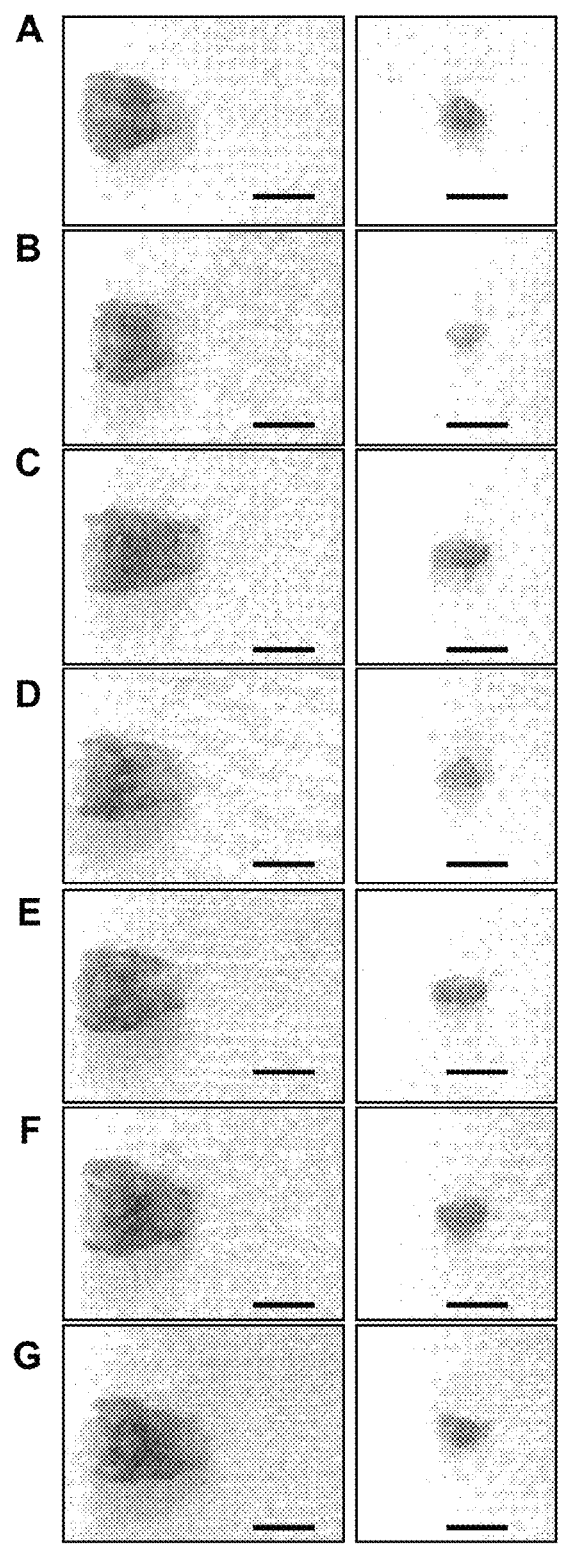
FIG. 3 shows an image of thyroid extracted from both intact control rat and LT4-induced hyperthyroidism rat.

A=Intact control rats
B=PTU treated control rats
C=LT4 0.5 mg/kg treated rats
D=LF 250 mg/kg treated rats
E=BH 500 mg/kg treated rats
F=BH 250 mg/kg treated rats
G=BH 125 mg/kg treated rats

BEST MODE FOR CARRYING OUT THE INVENTION

The present invention provides a pharmaceutical composition for preventing or treating thyroid diseases, comprising an extract from *Lonicera caerulea L. car. Edulis* fruits as an active ingredient.

As used herein, the term "*Lonicera caerulea L. car. edulis*" refers to a dicotyledonous plant of the family Dipsacales of the Order caprifoliaceae. It is a deciduous shrub that grows to 1.5 m, is densely branched, and has shield-shaped bracts at nodes of twigs. The inner part of branches is white. The leaves are opposite, lanciform to elliptic and blunt- or sharp-ended, lack teeth on the margins, have short hairs on the margins and surface, and have many wooly hairs underneath. The flowers usually have short stalks, which arise from leaf axils, have trumpet-shaped creamy white corollas, and bloom in summer Each calyx is split like five toothed sepals. The corollas are yellowish white, cylindial campanulate, 1.2 cm to 1.5 cm long, and have slightly hairy form. Further, the stamens are shorter than styles and have no hairs, and the two ovaries are fused together. "*Lonicera caerulea L. car. edulis*" is known as an arctic plant that is widespread in Siberia, Sakhalin, the Northern region of China, Tibet, North Korea, and elsewhere.

*Lonicera caerulea L. car. Edulis* fruits are oval- or nearly circular-shaped, ripen to purplish black between July and October, and are covered with white powder. With respect to the pharmacological activity of the *Lonicera caerulea L. car. Edulis*, the effects of the extract from *Lonicera caerulea L. car. Edulis* fruits on preventing and treating diseases, such as hepatitis, liver cirrhosis, or fatty liver, and the effects of *Lonicera caerulea L. car. Edulis* fruits on eliminating hangover are known. However, the use of the extract from *Lonicera caerulea L. car. Edulis* fruits for preventing or treating thyroid diseases, such as hypothyroidism, hyperthyroidism, thyroiditis, or thyroid nodule, is unknown and investigated by the present inventors for the first time. In the present invention, the *Lonicera caerulea L. car. Edulis* fruits sold commercially, may be purchased, or the ones that have been collected or cultivated in nature may be used.

In the present invention, the term "the extract from *Lonicera caerulea L. car. Edulis* fruits", which is obtained by extracting from *Lonicera caerulea L. car. Edulis* fruits, has effects on controlling the thyroid function. The extract from *Lonicera caerulea L. car. Edulis* fruits is obtained by the extraction process using water, organic solvents, or the mixture thereof with the shredded products of *Lonicera caerulea L. car. Edulis* fruits, and may include the extract, powder of the extract, and all forms formulated therefrom. Further, as for the extraction methods, hot water extraction, enfleurage extraction, reflux extraction or ultrasonic extraction may be utilized, but the methods are not limited thereto.

Water, organic solvents, and the mixture thereof may preferably be used for extraction to obtain the extract from *Lonicera caerulea L. car. Edulis* fruits.

When organic solvents are used for extraction, although not limited to the following, specific examples including methanol, ethanol, isopropanol, butanol, ethylene, acetone, hexane, ether, chloroform, ethyl acetate, butyl acetate, dichloromethane, N,N-dimethylforamide (DMF), dimethyl sulfoxide (DMSO), 1,3-butylene glycol, propylene glycol, or organic solvents that are the mixture thereof may be used. The extraction may be carried out at room temperature or heated temperature under the conditions that prevent the destruction of the active ingredient of crude drug or minimize such destruction. Since the degree of extraction and loss of an active ingredient may vary depending on the organic solvent used for extraction, appropriate organic solvents should be selected and used.

The extraction method may further include a step of filtering the extract to eliminate floating solid particles. The particles may be removed using cotton, nylon, ultrafiltration, freezing filtration, centrifugation and the like, but the present invention is not limited to the examples.

The concentration of the extract may be performed utilizing reduced pressure, reverse osmosis, and the like. The drying step after concentration includes freeze drying, vacuum drying, hot air drying, spray drying, drying under reduced pressure, foam drying, high frequency drying, infrared drying, and the like, but the present invention is not limited to the examples. If desired, a step of grinding the final dried extract may be further included.

In addition, the extraction method may carry out a further fractionation process. For example, the extract is suspended in distilled water and extracted using non-polar organic solvent, such as hexane, ether, dichloromethane, chloroform, ethyl acetate, or the mixture thereof to separate and obtain a non-polar solvent-soluble layer. The obtained non-polar solvent-soluble layer may be concentrated and/or dried.

For example, the extract of the present invention may be obtained by hot water extraction, enfleurage extraction, ultrasonic extraction or reflux extraction, preferably reflux extraction, using water, $C_1$ to $C_4$ lower alcohol or a solvent mixture thereof weighing 5 to 25 times, preferably 7 to 15 times as much as the dry weight of *Lonicera caerulea L. car. Edulis* fruits, which provides the extract from *Lonicera caerulea L. car. Edulis*. The extraction may be performed at 20° C. to 100° C., preferably 60° C. to 100° C., for a period ranging from 0.5 hours to 2 days, preferably 1 hour to 1 day, and may be serially performed 1 to 5 times, preferably 2 to 3 times. In addition, the extract may be passed through filter paper. The filtrate may be concentrated under reduced pressure utilizing a rotary vacuum concentrator at 20° C. to 100° C., preferably 50° C. to 70° C., and dried, thereby yielding the extract from *Lonicera caerulea L. car. Edulis* fruits in powder form according to the present invention. The extract from *Lonicera caerulea L. car. Edulis* fruits in the powder form may be used as it is or after being dissolved in a solvent at a pre-determined concentration.

In an embodiment of the present invention, by using water or mixed solvent containing water and alcohol as the solvent for extraction, 100 g of ground *Lonicera caerulea L. car. Edulis* fruits was added to 1 L of distilled water or 25% ethanol aqueous solution and agitated well. The resulting solution was extracted under reflux extraction for three hours at extraction temperature ranging from 80° C. to 95° C. and the extract was isolated. The obtained extract was concentrated under reduced pressure at temperature ranging from 55° C. to 65° C. and lyophilized, thereby yielding the powder extract of herbal composition (Example 1).

The extract from *Lonicera caerulea L. car. Edulis* fruits may contain betaine.

As used herein, the term "betaine", which is a collective term for trialkylamine, may chemically include amphoteric electrolytes that contain quaternary ammonium. Betaine is known to have bioactivity, such as lipotropic action, anti-hypertension, anti-blood glucose, visual recovery, detoxification, and cell cloning by stimulating methionine synthesis via methyl group donation. The extract from *Lonicera caerulea L. car. Edulis* fruits may contain such betaine, and its content may contain from 1% to 10%, preferably contain from 3% to 5%.

Because the extract from *Lonicera caerulea L. car. Edulis* fruits have an activity for improving thyroid function, the extract may be usd for preventing or treating thyroid diseases, such as hypothyroidism, hyperthyroidism, thyroid nodule, or thyroiditis. Further, the extract from *Lonicera caerulea L. car. Edulis* fruits may be used as supplements to increase the function of therapeutic agents for treating thyroid diseases for patients who are receiving treatment for thyroid diseases.

As used herein, the term "thyroid diseases" includes all the diseases caused by thyroid function defects. The thyroid diseases include diseases caused by the imbalance of thyroid hormone production from functional defects in thyroid gland itself, pituitary gland producing thyroid stimulating hormone (TSH), and hypothalamus, which control the pituitary gland through thyrotropin-releasing hormone (TRH); includes thyroid cancer or thyroid nodule; and thyroiditis. Specific examples include hypothyroidism, hyperthyroidism, thyroid nodule, thyroiditis, thyroid cancer, and thyrotoxicosis, but are not limited thereto.

Thyroid diseases of the present invention may preferably be hypothyroidism, hyperthyroidism, thyroid nodule, or thyroiditis.

The term "hypothyroidism" may refer to a state in which the thyroid hormone concentration is decreased or depleted in vivo because of the insufficient production of thyroid hormone in thyroid. The causes can be classified into the case where the thyroid hormone production is decreased due to the problems in thyroid itself and the case where the thyroid hormone production is decreased due to the problems in signaling, which enables hormone production in thyroid. The most common cause is the decreased thyroid hormone production in thyroid itself, which is caused by Hashimoto's thyroditis (autoimmune thyroditis). Hypothyroidism may also occur due to the non-secretion of TSH in the case of hypopituitarism. Symptoms of hypothyroidism include chronic fatigue, loss of apetitite, weight gain, poor ability to tolerate cold, and constipation.

The diagnosis of hypothyroidism is conducted by measuring the thyroid hormone concentration in blood through the blood test. In the case of hypothyroidism, the thyroid hormone (T4 or T3) concentration is measured lower than normal.

The term "hyperthyroidism" may refer to a state in which thyrotoxicosis occurs due to hormone secreted from thyroid (T3 or T4) is excessively secreted by certain causes. The main cause of hyperthyroidism is Grave's disease, and additionally, the oversecretion of TSH from pituitary adenoma or excessive intake of thyroid hormones may be other causes. Symptoms of hyperthyroidism include weight loss, tachycardia, palpitation, essential tremor, fatigue, anxiety, nervousness, muscle paralysis, dry eye syndrome, and keratitis. The diagnosis of hyperthyroidism is conducted by measuring the thyroid hormone concentration in blood through the blood test, and the thyroid hormone (T4 or T3) concentration is measured higher than normal.

The term "thyroid nodule", includes a formation of lumps, which arise from the enlargement of certain part of the tissue because of hyperplasia of thyroid cells. Thyroid nodule, which is one of the most common endocrine diseases, is known to be clinically occurred in 4% to 7% of adults.

Thyroid nodule may be classified into hyperplastic nodule, colloid nodule, inflammatory nodule, cystic nodule, and tumorigenic nodule including thyroid cancer based on the causes and histological characteristics. Hyperplastic nodule, a typical positive nodule, is known to occur because of environmental factors that induce thyroid cell proliferation such as iodine insufficiency. There are colloid nodules formed by the accumulation of liquid ingredients called colloid produced in thyroid cells, thyroiditis (inflammatory) nodule formed by the growth of lymphocytic thyroiditis in nodule form, and a type of cystic nodule caused by necrosis and denaturation of the existing nodule. In the case of tumorigenic nodule, such as malignant nodule (thyroid cancer), various gene modifications are identified as the cause of the disease.

The term "thyroiditis", which includes various forms of inflammatory diseases ranging from acute bacterial infection to chronic autoimmune thyroiditis, may be classified into acute thyroiditis, subacute thyroiditis, chronic lymphocytic thyroiditis, and painless thyroiditis based on the symptoms complained by patients and causes of the disease. While all the causes may vary depending on each thyroiditis, 1) acute thyroiditis is caused by the invasion of bacteria or microorganisms into existing patients suffering from thyroid diseases, 2) for subacute thyroiditis, although the causes are not well-known, the history of upper respiratory tract infection including cold is observed in many patients suffering from subacute thyroiditis, 3) painless thyroiditis is predicted to be a modified form of Hashimoto's thyroiditis, 4) postpartum thyroiditis, which is a type of painless thyroiditis, occurs after delivery; and 5) chronic lymphocytic thyroiditis (Hashimoto's thyroiditis) is a type of an autoimmune disease.

As for the symptoms, 1) in acute thyroiditis, pain and hot flash around infected site and change in skin color may appear. 2) The rest of the symptoms from subacute thyroiditis except pain (symptoms of painless thyroiditis and symptoms of Hashimoto's thyroiditis) are based on the condition of thyroid hormone. All the symptoms of thyrotoxicosis (symptoms shown in hyperthyroidism, such as palpitation, weight loss, and the like) and the symptoms of hypothyroidism (weight gain, edema, fatigue, and constipation) may appear.

The term "thyroid cancer" includes cancer formed within thyroid, and is classified into papillary carcinoma, follicular carcinoma, medullary carcinoma, and anaplastic cancer (undifferentiated carcinoma) based on histological shapes, progenitor cells of cancer, and the degree of differentiation. When thyroid nodule is determined as malignant nodule in general, it is called thyroid cancer.

Further, the composition comprising the extract from *Lonicera caerulea L. car. Edulis* fruits of the present invention have effects on inhibiting or improving defects in reproductive organs that can be caused by thyroid defects as well as preventing or treating thyroid diseases effectively.

Specifically, testis, which performs two physiologically important high energy required-activities, such as reproductive hormone synthesis (steroidogenesis) and sperm generation (spermatogenesis), is known to be vulnerable in peroxidative agents compared to other organs. Therefore, it is known that oxidative stress of testis is an important factor for male infertility at present (Reprod Feral Dev. 1994.6: 19-24; J Androl. 1996; 17:449-54) and that the number of sperms is changed based on the thyroid condition (Endocrinology. 1991; 129:244-8; New Engl J Med. 1984; 311:1353-62). Accordingly, there is a close relationship between the thyroid hormone content and male infertility.

As described above, the testis, which is a representative organ influenced by thyroid hormone, is known to accompany atrophy along with the decreased level of testosterone and dihydrootestosterone (DHT), which are male hormones, and the increased level of follicle-stimulating hormone (FSH) (Andrologia. 2003; 35:131-40; Gen Comp Endocrinol. 2008a, 156:63-70).

In one embodiment of the present invention, besides the recovery of thyroid function, the result of administering the extract from *Lonicera caerulea L. car. Edulis* fruits to the hypothyroidism animal model prepared by PTU administration are as follows. (1) it was confirmed that the weights of testis, epididymis, and prostate, which were reduced because of thyroid function decreased by PTU administration, were increased effectively, (2) the reduced content of male hormone was also increased, (3) the diameter of epididymal duct head, which was reduced because of atrophy, was increased, and the increased ratio of epididymal duct was decreased; and (4) it was confirmed that the average diameter of seminiferous tubules, which was reduced because of atrophy, was increased, and the decreased ratio of the seminiferous tubules between stages I to II was increased. (5) Further, it was confirmed that thickness of prostate duct epithelium, which was reduced because of atrophy, was increased, and the increased ratio of prostate duct was also decreased. Consequently, it is suggested that the PTU-induced reproductive organ defects and antioxidant defense system deteriorated by PTU were effectively improved by the extract from *Lonicera caerulea L. car. Edulis* fruits.

On the other hand, it was observed that the defects in reproductive organs including testis, prostate, and epididymis became rather deteriorated in LT4 treated rats, and the deterioration of the reproductive organ defects was recognized. Accordingly, unlike LT4, which has therapeutic activity for hypothyroidism, but involves the reproductive organ defects as side effects, the extract from *Lonicera caerulea L. car. Edulis* fruits of the present invention does not deteriorate the reproductive organ defects accompanied by hypothyroidism, but rather inhibit or treat the defects, and bring about the effects for treating hypothyroidism effectively. Therefore, the composition of the present invention may be effectively used as improving agents for thyroid function or therapeutic agents for hypothyroidism without any side effects.

As used herein, the term "prevention" refers to all the activities that inhibit or delay the occurence of the thyroid diseases by administering the composition, and the term "treatment" refers to all the activities of which symptoms caused by the thyroid diseases become improved or beneficially changed by the composition.

The pharmaceutical composition comprising the extract from *Lonicera caerulea L. car. Edulis* fruits of the present invention may further include appropriate carriers, excipients, or diluents that are generally used for the preparation of the pharmaceutical composition. Herein, the extract content of *Lonicera caerulea L. car. Edulis* fruits included in the composition is not specifically limited to the examples, but may contain an amount of 0.01 wt % to 100 wt %, preferably 1 wt % to 80 wt % by weight based on the total weight of the composition.

The pharmaceutical composition may have any one of formations selected from the group consisting of tablets, pills, powders, granules, capsules, suspensions, liquid medicine, emulsions, syrups, sterilized aqueous solutions, non-aqueous solutions, suspensions, emulsions, lyophilized products, and suppositories, and may be in oral or parenteral formation. When formulated, the composition is prepared by generally using diluents or excipients including fillers, bulking agents, binding agents, wetting agents, disintegrating agents, surfactants and the like. Solid formulations for oral administration include tablets, pills, powders, granules, capsules, and the like. Such solid formulations are prepared by mixing at least one compound with at least one excipient, for example, starch, calcium carbonate, sucrose or lactose, gelatin, and the like. Further, lubricants, such as magnesium stearate, talc and the like are used in addition to simple excipients. Liquid formulations for oral administration include suspensions, liquid medicine, emulsions, syrups, and the like, but may also include various excipients, for example, wetting agents, sweetening agents, air fresheners, preserving agents, and the like, in addition to generally used simple diluents, such as water and liquid paraffin. Formulations for parenteral administration include sterilized aqueous solutions, non-aqueous solvents, suspensions, emulsions, lyophilization agents, and suppositories. As non-aqueous solvents and suspensions, propylene glycol, polyethylene glycol, vegetable oil including olive oil, ester capable of injection including ethyl oleate and the like may be used. As a base material for the suppositories, witepsol, macrogol, tween 61, cacao butter, laurinum, glycerogelatin and the like may be used.

The composition of the present invention may be administered with a pharmaceutically effective amount.

As used herein, the term "pharmaceutically effective amount" refers to an amount sufficient for treating diseases at a reasonable benefit/risk ratio applicable for medical treatment, and an effective dosage amount may be determined depending on types of subject, severity of diseases, age, gender, type of diseases, drug activity, sensitivity to drugs, administration time, administration routes and excretion rates, treatment duration, elements including simultaneously used drugs, and elements well-known in other medical fields. The composition of the present invention may be administered as an individual therapeutic agent or in combination with other therapeutic agents, and may be administered sequentially or simultaneously with conventional therapeutic agents. The composition of the present invention may also be administered in single or multiple doses. Taking all factors into consideration, it is important to conduct administration with the minimum of doses that is capable of realizing the greatest effects with no adverse effects, such doses being readily determined by one of ordinary skill in the art. A preferred dose of the composition of the present invention may vary based on the condition and weight of the patients, severity of the disease, drug form, administration routes and period. A total amount for daily usage may be determined by the doctor in charge within the right range of medical determination, but in general, the amount ranging from 0.001 mg/kg to 1000 mg/kg, preferably from 0.05 mg/kg to 200 mg/kg, more preferably from 0.1 to 100 mg/kg may be administered once to several times a day. As long as the composition is a subject with the purpose of preventing or treating thyroid diseases, the subject is not particularly limited, and anything may be applicable. For example, any non-human animals, such as monkeys, dogs, cats, rabbits, guinea pigs, rats, mice, cows, sheep, pigs, and goats, humans, birds, fish and the like may be used, and if the administration method is the conventional method in the art, the method is included without any limitations. For example, the composition may be administered by oral, rectal or intravenous, intramuscular, subcutaneous injection, and by injection in dura mater in uterus or brain blood vessel.

In one embodiment of the present invention, a clinical trial was conducted by enabling three volunteers suffering from hypothyroidism, thyroiditis, or malignant tumor nodule to be orally dosed with 3 g of the extract from *Lonicera caerulea L. car. Edulis* fruits twice a day. As a result of the diagnosis for the thyroid function tests (T3, T4, Free T4, and TSH), hypothyroidism patients showed that thyroid function was recovered to normal after 30-day ingestion. As a result of observing condition change of the nodules by ultrasound, it was confirmed that patients suffering from thyroiditis or malignant thyroid nodule showed that malignant tumor (thyroid cancer) disappeared and the nodule size was decreased after 1-year ingestion of the extract from *Lonicera caerulea L. car. Edulis* fruits (Experimental Example 2).

Further, as a result of administering the extract from *Lonicera caerulea L. car. Edulis* fruits to a hyperthyroidism animal model induced by levothyroxine (LT4), it was confirmed that (1) decreased weight and thyroid weight were increased and (2) decreased level of TSH in blood serum was increased and increased levels of T3 and T4 were decreased (Experimental Example 3).

Further, as a result of administering the extract from *Lonicera caerulea L. car. Edulis* fruits to a hypothyroidism animal model induced by propylthiouracil (PTU), it was confirmed that (1) decreased weight was increased, (2) increased thyroid weight was decreased, and (3) increased level of TSH in blood serum was decreased along with the increase of the decreased levels of T3 and T4 (Experimental Example 4).

The result suggests that the composition including the extract from *Lonicera caerulea L. car. Edulis* fruits of the present invention is useful for preventing and treating the thyroid diseases.

The present invention provides a food composition for improving thyroid function, comprising the extract from *Lonicera caerulea L. car. Edulis* fruits as an active ingredient.

*Lonicera caerulea L. car. Edulis* fruits, the extract from *Lonicera caerulea L. car. Edulis* fruits, and thyroid are the same as described above.

Specifically, the extract of the present invention may be added to the food composition for the purpose of improving thyroid function. In particular, the extract from *Lonicera caerulea L. car. Edulis* fruits of the present invention improves the conditions caused by defects or damages in thyroid function. Therefore, the extract may be added to the food composition for the purpose of preventing or treating hypothyroidism, thyroiditis, thyroid nodule, or thyroid cancer. Further, since the extract from *Lonicera caerulea L. car. Edulis* fruits have been obtained from natural products, the composition including the extract is safe and does not cause side effects or resistance thereto and thus, may be used as the food composition. In one embodiment, as the result of the cell toxicity test for the extract from *Lonicera caerulea L. car. Edulis* fruits of the present invention, it was confirmed that toxicity was not induced (Experimental Example 1).

Further, the composition may be applied to humans, as well as livestocks including cows, horses, sheep, pigs, goats, camels, antelopes, and dogs, in which thyroid function may be reduced, but there are no specific limitations thereto.

The extract from *Lonicera caerulea L. car. Edulis* fruits may contain an amount of 0.01 wt % to 100 wt %, more preferably 1 wt % to 80 wt % by weight based on the total weight of the food composition. When the food is a drink, the extract from *Lonicera caerulea L. car. Edulis* fruits is present in an amount of 1 g to 30 g, preferably 3 g to 20 g, in 100 ml of the drink. Further, the composition may include additional ingredients, which are commonly used for the food composition to enhance smell, taste, and vision. For example, vitamins A, C, D, E, $B_1$, $B_2$, $B_6$, $B_{12}$, niacin, biotin, folate, panthotenic acid, and the like may be included.

Further, minerals, such as zinc (Zn), iron (Fe), calcium (Ca), chromium (Cr), magnesium (Mg), manganese (Mn), copper (Cu) and the like may be included. In addition to this, amino acids, such as lycine, tryptophan, cysteine, valine and the like may be included. Further, food additives, such as antiseptics (e.g., potassium sorbate, sodium benzoate, salicylic acid, sodium dehydroacetate, etc.), disinfecting agents (e.g., bleaching powder, high-grade bleaching powder, sodium hypochlorite, etc.), antioxidants (butylated hydroxyanisole (BHA), butylated hydroxytoluene (BHT), etc.), colorants (e.g., tar dye, etc.), color fixing agents (e.g., sodium nitrate, sodium nitrite, etc.), bleaching agents (e.g., sodium sulfite), seasoning agents (e.g., MSG, sodium glutamate, etc.), sweeteners (e.g., dulcin, cyclamate, saccharin, sodium, etc.), flavoring agents (e.g., vanillin, lactone, etc.), blowing agents (e.g., alum, D-potassium hydrogen tartrat, etc.), fortifying agents, emulsifying agents, thickeners (thickening agents), film-forming agents, gum bases, antifoaming agents, solvents, and conditioners may be supplemented. When the extract from *Lonicera caerulea L. car. Edulis* fruits of the present invention is used as food additives, the extract itself may be added or used in combination with other food or ingredients, and then used based on conventional methods. The mixing amount of the active ingredients may be determined appropriately based on the intended use.

Food types of the present invention do not have any particular limitations. The examples of food that may contain the composition that has the extract from *Lonicera caerulea L. car. Edulis* fruits as an active ingredient include confectioneries, drinks, alcoholic beverages, fermented foods, canned foods, processed milk products, processed meat products, noodles and the like. Confectioneries include biscuits, pies, cakes, breads, chocolate, candies, jellies, gums, cereals (including substitute food for a meal, such as crop flakes), ice cream and the like. Drinks include carbonated drinks, functional ionic drinks, juices (e.g., apple, pear, grape, aloe, tangerine, peach, carrot, tomato juices, etc.), rice nectar (Korean traditional sweet rice drink made from fermented rice), energy drinks, tea, and the like. Herein, the drinks may contain pulps for preparing natural fruit juice, fruit juice drinks, vegetable juice drinks, and the like. Alcoholic beverages include cheongju (Korean traditional clear rice wine, whisky, soju (Korean traditional liquor), beer, wine, fruit wine, and the like. Fermented foods include soy sauce, soybean paste, hot pepper paste, and the like. Canned products include marine canned products (e.g., canned tuna, mackerel, saury, top shell (Turbo cornutus), etc.), canned stock farm products (e.g., canned beef, pork, chicken, turkey, etc.), and canned agricultural products (e.g., canned corn, peaches, pineapples, etc.). Processed milk products include cheese, butter, yogurt, and the like. Processed meat products include pork cutlets, beef cutlets, chicken cutlets, sausages, tangsuyuk (fried pork with sweet and sour sauce), nuggets, neobiani (Korean grilled and sliced beef), and the like. Noodle products include sealed and packaged wet noodles, ramen, and the like. In addition, the composition may be used in retort food, soups, and the like. Further, foods used for animal feeds are also included.

Further, food may be prepared in the form of tablets, granules, capsules, solution in liquid phase, pills and the like based on the known preparation methods. There are no specific limitations for other ingredients except for the fact the extract from *Lonicera caerulea L. car. Edulis* fruits of the present invention is included, and many conventional flavoring agents or natural carbohydrates may be further included as additional ingredients.

Further, the present invention provides a method for preventing, improving or treating the thyroid diseases, including administrating the extract from *Lonicera caerulea L. car. Edulis* fruits to a subject who is suspected to have the thyroid diseases.

Specifically, the method for prevention, improvement or treatment of the present invention includes administering a pharmaceutically effective amount of the extract from *Lonicera caerulea L. car. Edulis* fruits to a subject who is suspected to have thyroid diseases. The subject refers to all the animals including humans in which the thyroid diseases have occurred or may occur. The extract from *Lonicera caerulea L. car. Edulis* fruits may be administered in the form of the pharmaceutical composition. The extract may also be administered by the method of oral administration or parenteral administration. Further, the preferable administering dose of the extract from *Lonicera caerulea L. car. Edulis* fruits may vary based on the condition and weight of the patients, severity of the disease, form of drugs, and administration routes and period, and may be determined accordingly by one of ordinary skill in the art.

The present invention provides the use of the extract from *Lonicera caerulea L. car. Edulis* fruits for the preparation of medicament for prevention or treatment of thyroid diseases. Further, the present invention provides the use of the extract from *Lonicera caerulea L. car. Edulis* fruits for the preparation of food for prevention or treatment of the thyroid diseases.

The explanation for the extract from *Lonicera caerulea L. car. Edulis* fruits is the same as described above. The fact that the extract may be included in the pharmaceutical composition for preventing or treating the thyroid diseases and the extract may be included in the food composition for preventing or improving thyroid diseases as active ingredients and used is also same as described above.

[Mode For Carrying Out The Invention]

Hereinafter, the present invention will be described in details with reference to the following Examples. However, these Examples are for illustrative purposes only, and the scope of the present invention is not limited to these Examples.

EXAMPLE 1

Preparation of the Extract from *Lonicera caerulea L. car. Edulis* Fruits

EXAMPLE 1-1

Hot Water Extraction Method Using Water Solvents

*Lonicera caerulea L. car. edulis* fruits, which was directly harvested from the Heilongjiang region in China, were dried and used for the experiment.

Specifically, 100 g of ground *Lonicera caerulea L. car. edulis* fruits was added to 1 L of distilled water and agitated well. The resulting solution was extracted under reflux extraction for 3 hours at extraction temperature ranging from 90° C. to 95° C. and the extract was isolated. The obtained extract was concentrated under reduced pressure at temperature ranging from 55° C. to 65° C. and lyophilized, thereby yielding 21.2 g of the extract powder of the herbal composition.

EXAMPLE 1-2

Hot Water Extraction Method Using Mixed Solvents Containing Water and Alcohol

As in Example 1-1, 1 L of 25% ethyl alcohol was added to 100 g of ground *Lonicera caerulea L. car. edulis* fruits and agitated well. The resulting solution was extracted under reflux extraction for 3 hours at heated extraction temperature ranging from 80° C. to 90° C. and the extract was isolated. The obtained extract was concentrated under reduced pressure at temperature ranging from 55° C. to 65° C. and lyophilized, thereby yielding 19.5 g of the extract powder of the herbal composition.

EXPERIMENTAL EXAMPLE 1

Toxicity Test

The hot water extract or hot water alcohol extract prepared in Example 1 was dissolved in distilled water and 500 mg/kg of each was administered to each mouse (10 per group), respectively. Then, the mice were monitored for 7 days. No death was observed, indicating that the extract was not toxic.

EXPERIMENTAL EXAMPLE 2

Effects on Treating Hypothyroidism, Thyroiditis, and Thyroid Nodule by the Extract from *Lonicera caerulea L. car. edulis* Fruits Three volunteers suffering from hypothyroidism, thyroiditis, or thyroid nodule were orally dosed with 3 g of the extract from *Lonicera caerulea L. car. Edulis* fruits twice a day. Information for each volunteer and the results from before and after the oral dosage were shown below.

(1) Subject 1: Female, Age Thirty-Nine
A. Symptoms Before Administration:
Complaining of fatigue and lethargy due to hypothyroidism
T4 (Thyroxine): 4.98 (low)
TSH (Thyroid-stimulating hormone): 19.17 (high)
B. After Administration:
After 30-day administration, Free T4: 1.33 (normal), TSH: 1.97 (normal) recovery
(2) Subject 2: Female, Age Forty-Nine
A. Symptoms Before Administration:
Symptoms of Edema and chronic fatigue due to hypothyroidism
Free T4: 0.85 (low), TSH: 100 (high)
B. After Administration:
After 30-day administration, Free T4: 1.51 (normal), TSH: 0.918 (normal) recovery
(3) Subject 3: Female, Age Sixty
A. Symptoms Before Administration:
Thyroiditis showing sporadic nodules in thyroid, malignant tumor
B. After Administration:
After 1-year administration, nodules in both left and right lobes of the thyroid have decreased and malignant tumor has disappeared
T3 (tri-iodothyronine): 1.34 (normal), Free T4: 1.29 (normal), TSH: 0.973 (normal)

As indicated from the result, the diagnostic result of thyroid function tests (T3, T4, Free T4, and TSH) showed that thyroid function was recovered to normal after 30-day ingestion in hypothyroidism patients. As a result of observing the condition change of the nodules by ultrasound, it was confirmed that malignant tumor (thyroid cancer) was disappeared and the size of the nodules was decreased after 1-year ingestion of the extract from *Lonicera caerulea L. car. Edulis* fruits in patients suffering from thyroiditis or malignant thyroid nodule.

The results suggest that the extract from *Lonicera caerulea L. car. Edulis* fruits is useful for treating thyroid diseases, such as hypothyroidism, hyperthyroidism, thyroid nodule, or thyroiditis.

EXPERIMENTAL EXAMPLE 3

Effects on Treating Hyperthyroidism by the Extract from *Lonicera caerulea L. car. Edulis* Fruits (1) Preparation of Hyperthyroidism Animal Model
A. Experimental Animals Total number of 150 male SPF. VAF Outbred-Rats, Crl: CD [Sprague-Dawley, SD] rats (6 weeks old, OrientBio, Seungnam, Korea) were prepared and refined for 8 days in a laboratory environment. After that, rats with consistent weight (average: 233.70 g±10.47 g, 217 g to 252 g) were selected, and 8 rats per group (total of 56 rats) were used for the experiment. In the present invention, all the experimental animals were treated according to animal ethics of the animal experimentation ethics committee of Daegu Haany University. The experiment was conducted after pre-approval.

B. Induction of Hyperthyroidism

Based on conventional methods known in the art (Clin Exp Pharmacol Physiol. 2007 November; 34(11):1217-9, etc.), a hyperthyroidism animal model was prepared by administering LT4 (levothyroxine). Specifically, hyperthyroidism was induced by dissolving 3 mg of LT4 into 10 ml of saline solution and subcutaneously injecting the capacity of 1 ml/kg into dorsal neck of the animal model once everyday for a period of 27 days. On the other hand, in the intact control group, the same amount of saline solution instead of LT4 was administered for the same period in the same manner as described above (FIG. 1).

(2) Effects on Treating Hyperthyroidism by Administration of the Extract from *Lonicera caerulea L. car. Edulis* Fruits A. Administration of Experimental Substance Targeting the hyperthyroidism animal prepared as above, 500, 250, and 125 mg/kg of the extract from *Lonicera caerulea L. car. Edulis* fruits (BH) prepared in Example 1-1 were dissolved in sterilized distilled water, respectively, and the capacity of 5 ml/kg was orally administered forcibly once a day from Day 12 to Day 15 since the treatment.

On the other hand, Lonicerae Flos aqueous hot water extract (LF), an experimental group, was also dissolved in sterilized distilled water, and the capacity of 250 mg/kg was orally administered for the same period in the same manner as described above. 10 mg/kg of PTU was dissolved in saline solution, and the capacity of 1 ml/kg was intraperitoneally administered for the same period in the same manner as described above (Table 1, FIG. 1).

TABLE 1

| Group Classification | (Total: 7 groups; 8 rats per group) |
|---|---|
| Control Groups | |
| Intact control | Saline solution administered instead of LT4, and distilled water orally administered rats |
| LT4 treatment | LT4 subcutaneously administered and distilled water orally administered rats |
| Experimental Groups | |
| PTU treatment | LT4 subcutaneously administered and PTU (10 mg/kg) intraperitoneally administered rats |
| LF 250 mg/kg | LT4 subcutaneously administered and LF (250 mg/kg) orally administered rats |
| BH treatment Groups | |
| 500 mg/kg | LT4 subcutaneously administered and BH (500 mg/kg) orally administered rats |
| 250 mg/kg | LT4 subcutaneously administered and BH (250 mg/kg) orally administered rats |
| 125 mg/kg | LT4 subcutaneously administered and BH (125 mg/kg) orally administered rats |

Next, the effects on treating hyperthyroidism was confirmed by observing the weight change, thyroid weight change, content change in blood thyroid hormone (TSH, T3, and T4), and histopathological change in the thyroid (the total thickness of thyroid in which the cells have been cut, average diameter of thyroid follicle, and thickness of thyroid epithelium) of the rats for each group.

B. Change in Weight

In the LT4 administered control group, a significant decrease in weight was shown compared to the intact control group not administered with LT4.

On the other hand, compared to the LT4 control group, the weight was considerably increased in PTU (10 mg/kg) intraperitoneally administered group, LF (250 mg/kg) orally administered group, and 500 mg/kg, 250 mg/kg, and 125 mg/kg BH orally administered group, from 5, 14, 5, 5, and 10 days after administration, respectively. Specifically, activities in the BH (500 mg/kg and 250 mg/kg) administered groups were superior to the LF (250 mg/kg) administered group, which was an experimental group, since the BH administered group showed a considerable increase in weight about 9 days earlier compared to the LF administered group (Table 2).

TABLE 2

| | Body weight gains during | | |
|---|---|---|---|
| Groups | 12 days of LT4 pretreatment | 15 days of PTU and herbal extracts treatment | 27 days of total experiments |
| Controls | | | |
| Intact | 86.00 ± 6.63 | 97.13 ± 10.48 | 183.13 ± 11.36 |
| LT4 Reference | 56.63 ± 6.46$^d$ | 26.88 ± 4.64$^a$ | 29.75 ± 6.07$^a$ |
| PTU 10 mg/kg | 54.50 ± 13.15$^d$ | 58.75 ± 15.04$^{ab}$ | 113.63 ± 24.49$^{ab}$ |
| LF 250 mg/kg | 55.00 ± 9.71$^d$ | 7.38 ± 14.91$^{ab}$ | 62.38 ± 17.30$^{ab}$ |

TABLE 2-continued

| | Body weight gains during | | |
|---|---|---|---|
| Groups | 12 days of LT4 pretreatment | 15 days of PTU and herbal extracts treatment | 27 days of total experiments |
| BH treated | | | |
| 500 mg/kg | 58.25 ± 12.99$^d$ | 44.50 ± 12.21$^{abc}$ | 102.75 ± 23.65$^{abc}$ |
| 250 mg/kg | 58.38 ± 6.52$^d$ | 35.25 ± 12.93$^{abc}$ | 93.63 ± 12.65$^{abc}$ |
| 125 mg/kg | 57.13 ± 11.03$^d$ | 18.50 ± 20.33$^{ab}$ | 75.63 ± 14.43$^{ab}$ |

Values are expressed as Mean ± S.D. of eight rats
LT4 = Levothyroxine
PTU = Propylthiouracil, 6-n-propyl-2-thiouracil
LF = *Lonicerae* Flos lyophilized aqueous extracts
BH = Blue honeysuckle lyophilized concentrated powder
$^a$p < 0.01 as compared with intact control by LSD test
$^b$p < 0.01 as compared with LT4 control by LSD test
$^c$p < 0.01 as compared with LF 250 mg/kg by LSD test
$^d$p < 0.01 as compared with intact control by MW test C. Change in the Weight of Thyroid On the final day of sacrifice, left thyroids of all the experimental animals were extracted and isolated and next, the weight was measured and designated as the absolute weight. In order to minimize the secondary change accompanied with the change in weight, relative thyroid gland weight (Absolute kidney weight/body weight at sacrifice ×100), which was the ratio of the absolute weight of the thyroid based on body weight, was calculated.

As a result, it was confirmed that a significant atrophy of the thyroid was shown in the LT4 administered control group compared to the intact control group not administered with LT4, and the absolute and relative thyroid weights were also considerably reduced.

On the other hand, a considerable increase of the absolute and relative thyroid weights was recognized in all the experimental groups including the PTU administered group and the BH treated group, respectively, compared to the LT4 control group. Specifically, the increment of the thyroid weight was considerably large in the BH (500 mg/kg, 250 mg/kg, and 125 mg/kg) administered groups compared to the LF (250 mg/kg) administered group (Table 3).

TABLE 3

| Groups | Absolute organ weights Thyroid gland (mg) | Relative organ weights (% of BW) Thyroid gland (mg/g of BW) |
|---|---|---|
| Controls | | |
| Intact | 9.50 ± 2.67 | 2.40 ± 0.66 |
| LT4 Reference | 2.88 ± 0.99$^f$ | 1.18 ± 0.39$^a$ |
| PTU 10 mg/kg | 8.88 ± 2.03$^h$ | 2.71 ± 0.64$^c$ |
| LF 250 mg/kg | 4.88 ± 1.13$^{fh}$ | 1.78 ± 0.46$^{bd}$ |

TABLE 3-continued

| Groups | Absolute organ weights Thyroid gland (mg) | Relative organ weights (% of BW) Thyroid gland (mg/g of BW) |
|---|---|---|
| BH treated | | |
| 500 mg/kg | 7.63 ± 1.69$^{hj}$ | 2.42 ± 0.59$^{ce}$ |
| 250 mg/kg | 7.25 ± 1.49$^{hj}$ | 2.38 ± 0.50$^{ce}$ |
| 125 mg/kg | 5.25 ± 1.39$^{fh}$ | 1.86 ± 0.55$^{d}$ |

Values are expressed as Mean ± S.D. of eight rats
LT4 = Levothyroxine
PTU = Propylthiouracil, 6-n-propyl-2-thiouracil
LF = Lonicerae Flos lyophilized aqueous extracts
BH = Blue honeysuckle lyophilized concentrated powder
BW = Body weights
$^a$p < 0.01 and $^b$p < 0.05 as compared with intact control by LSD test
$^c$p < 0.01 and $^d$p < 0.05 as compared with LT4 control by LSD test
$^e$p < 0.05 as compared with LF 250 mg/kg by LSD test
$^f$p < 0.01 and $^g$p < 0.05 as compared with intact control by MW test
$^h$p < 0.01 and $^i$p < 0.05 as compared with LT4 control by MW test
$^j$p < 0.01 and $^k$p < 0.05 as compared with LF 250 mg/kg by MW test D. Change in the Thyroid Hormone Content in Blood The TSH, T3, and T4 contents in blood were measured in the units including ng/ml or µg/ml by Gamma count Cobra II (Packard Co., IL, USA) utilizing Coat A count Total TSH, T3 or T4 kit (DPC, CA, USA), respectively, based on Radioimmunoassay method (Toxicol Sci 69(1): 79-91, 2002).

As a result, the TSH content in blood was considerably decreased and the T3 and T4 contents in blood were considerably increased in the LT4 administered group compared to the intact control group not administered with LT4.

On the other hand, a considerable increase in the TSH content and a considerable decrease in T3 and T4 contents were confirmed in all the experimental groups including PTU administered group and BH treated group, respectively, compared to LT4 control group. Specifically, a considerable increase in the TSH content and a considerable decrease in the T3 and T4 contents were confirmed in the BH (500 mg/kg, 250 mg/kg, and 125 mg/kg) administered groups (Table 4).

TABLE 4

| | Serum thyroid hormone levels | | |
|---|---|---|---|
| Groups | TSH (ng/ml) | Tri-iodothyronine (ng/ml) | Thyroxine (µg/ml) |
| Controls | | | |
| Intact | 1.71 ± 0.26 | 0.49 ± 0.15 | 47.08 ± 12.80 |
| LT4 Reference | 0.54 ± 0.11$^a$ | 2.03 ± 0.22$^a$ | 153.68 ± 21.71$^a$ |
| PTU 10 mg/kg | 1.37 ± 0.24$^{ac}$ | 0.80 ± 0.18$^{ac}$ | 71.30 ± 23.13$^{bc}$ |
| LF 250 mg/kg | 0.71 ± 0.10$^{ad}$ | 1.42 ± 0.24$^{ac}$ | 122.08 ± 11.89$^{ac}$ |
| BH treated | | | |
| 500 mg/kg | 0.98 ± 0.17$^{ace}$ | 0.90 ± 0.11$^{ace}$ | 91.54 ± 12.76$^{ace}$ |
| 250 mg/kg | 0.89 ± 0.11$^{ace}$ | 1.08 ± 0.09$^{ace}$ | 101.85 ± 17.23$^{acf}$ |
| 125 mg/kg | 0.76 ± 0.16$^{ad}$ | 1.29 ± 0.23$^{ac}$ | 116.12 ± 25.13$^{ac}$ |

Values are expressed as Mean ± S.D. of eight rats
LT4 = Levothyroxine
PTU = Propylthiouracil, 6-n-propyl-2-thiouracil
LF = Lonicerae Flos lyophilized aqueous extracts
BH = Blue honeysuckle lyophilized concentrated powder
TSH = Thyroid stimulating hormone
$^a$p < 0.01 and $^b$p < 0.05 as compared with intact control by LSD test
$^c$p < 0.01 and $^d$p < 0.05 as compared with LT4 control by LSD test
$^e$p < 0.01 and $^f$p < 0.05 as compared with LF 250 mg/kg by LSD test E. Histopathological Observation of Thyroid It was confirmed that the total thickness of thyroid and the thickness of thyroid follicular epithelium were considerably thin and the follicular diameter was considerably increased in the LT4 administered control group compared to the intact control group not administered with LT4. This suggests the atrophy of the thyroid follicle caused by the colloid substance accumulation in the follicle.

On the other hand, it was confirmed that the total thickness of thyroid and the thickness of follicular epithelium were considerably increased in all the experimental groups including the PTU administered group and BH treated group compared to the LT4 control group, and the average thyroid follicular diameter was considerably decreased. Specifically, the effects were even more noticeable in the BH (500, 250, and 125 mg/kg) administered groups compared to the LF 250 mg/kg administered group (Table 5).

TABLE 5

| | Thyroid glands | | |
|---|---|---|---|
| Groups | Total thickness (µm/central region) | Mean follicular epithelium thickness (µm/follicle) | Mean follicular thickness (µm/follicle) |
| Controls | | | |
| Intact | 1849.69 ± 185.36 | 23.16 ± 2.26 | 68.42 ± 10.54 |
| LT4 Reference | 1013.57 ± 132.09$^a$ | 4.50 ± 1.56$^g$ | 128.95 ± 15.03$^a$ |
| PTU 10 mg/kg | 1628.19 ± 174.84$^{ac}$ | 14.50 ± 2.84$^{gh}$ | 71.87 ± 12.05$^c$ |
| LF 250 mg/kg | 1207.25 ± 110.20$^{ac}$ | 7.51 ± 1.24$^{gh}$ | 106.57 ± 13.72$^{ac}$ |
| BH treated | | | |
| 500 mg/kg | 1583.65 ± 141.66$^{ace}$ | 14.67 ± 1.72$^{ghi}$ | 81.94 ± 10.62$^{bce}$ |
| 250 mg/kg | 1550.82 ± 133.99$^{ace}$ | 10.44 ± 1.77$^{ghi}$ | 83.96 ± 11.03$^{bce}$ |
| 125 mg/kg | 1258.18 ± 117.15$^{ac}$ | 7.91 ± 1.05$^{gh}$ | 95.85 ± 15.50$^{bc}$ |

Values are expressed as Mean ± S.D. of eight rats
LT4 = Levothyroxine
PTU = Propylthiouracil, 6-n-propyl-2-thiouracil
LF = Lonicerae Flos lyophilized aqueous extracts
BH = Blue honeysuckle lyophilized concentrated powder
$^a$p < 0.01 and $^b$p < 0.05 as compared with intact control by LSD test
$^c$p < 0.01 and $^d$p < 0.05 as compared with LT4 control by LSD test
$^e$p < 0.01 and $^f$p < 0.05 as compared with LF 250 mg/kg by LSD test
$^g$p < 0.01 as compared with intact control by MW test
$^h$p < 0.01 as compared with LT4 control by MW test
$^i$p < 0.01 as compared with LF 250 mg/kg by MW test

EXPERIMENTAL EXAMPLE 4

Effects on Treating Hypothyroidism by Administration of the Extract from *Lonicera caerulea L. car. Edulis* Fruits (1) Preparation of Hypothyroidism Animal Model A. Experimental Animals Experimental animals are the same as described in Experimental Example 3.

B. Induction of Hypothyroidism

Figure 5:
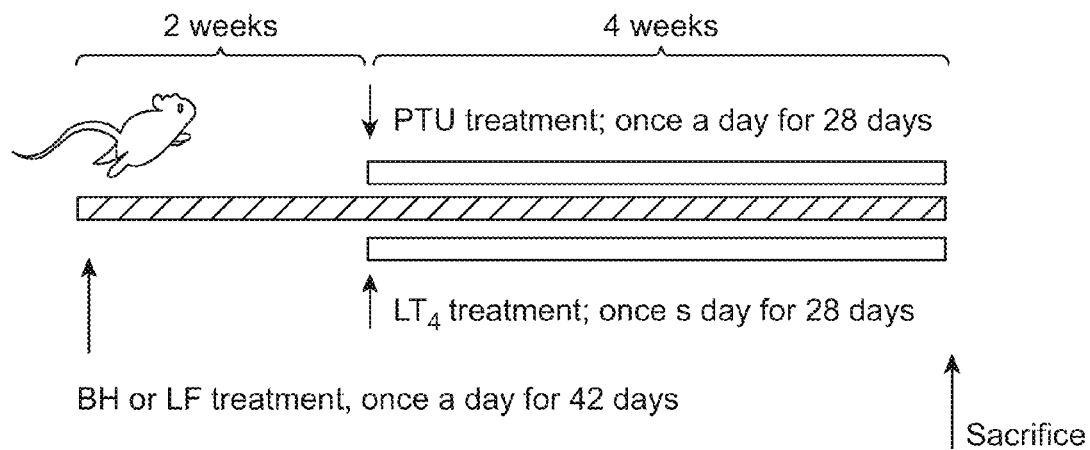
FIG. 5 shows a diagram that shows processes of Example 4 for observing effects on preventing or treating hypothyroidism by administering the extract from *Lonicera caerulea L. car. Edulis* to a PTU-induced hypothyroidism animal model.

Based on conventional methods known in the art (Neuro Endocrinol Lett. 1999; 20:311-14; Toxicol Sci. 2002; 69:79-91; Korean J Orient Physiol Pathol. 2010; 24:630-7), a hypothyroidism animal model was prepared by administering Propylthiouracil (PTU). Specifically, hypothyroidism was induced by dissolving 100 mg of PTU into 10 ml of saline solution and subcutaneously injecting the capacity of 1 ml/kg into dorsal neck of the animal model once everyday for a period of 28 days. On the other hand, in the intact control group, the same amount of saline solution instead of PTU was administered for the same period in the same manner as described above (FIG. 5).

(2) Effects on Treating Hypothyroidism by Administration of the Extract from *Lonicera caerulea L. car. Edulis* Fruits A. Administration of Experimental Substance Targeting the hypothyroidism animal prepared as above, 500, 250, and 125 mg/kg of the extract from *Lonicera caerulea L. car. Edulis* fruits (BH) prepared in Example 1-1 were dissolved in sterilized distilled water, respectively, and the capacity of 5 ml/kg was orally administered forcibly once a day for 42 consecutive days, 2 weeks prior to the PTU treatment. On the other hand, LF, an experimental group, was also dissolved in sterilized distilled water, and the capacity of 250 mg/kg was orally administered for the same period in the manner as described above.

0.5 mg/kg of LT4 was dissolved in saline solution, and the capacity of 1 ml/kg was intraperitoneally administered once a day for 28 consecutive days since the PTU treatment day in the same manner as described above (Table 6, FIG. 5).

TABLE 6

| Group Classification | (Total: 7 groups; 8 mice per group) |
|---|---|
| | Control groups |
| Intact control | Saline solution administered instead of PTU, and distilled water orally administered rats |
| PTU treatment | PTU subcutaneously administered and distilled water orally administered rats |
| | Experimental Groups |
| LT4 treatment | PTU subcutaneously administered and LT4 (0.5 mg/kg) intraperitoneally administered rats |
| LF 250 mg/kg | PTU subcutaneously administered and LF (250 mg/kg) orally administered rats |
| | BH treatment Groups |
| 500 mg/kg | PTU subcutaneously administered and BH (500 mg/kg) orally administered rats |
| 250 mg/kg | PTU subcutaneously administered and BH (250 mg/kg) orally administered rats |
| 125 mg/kg | PTU subcutaneously administered and BH (125 mg/kg) orally administered rats |

Next, the effects on treating hypothyroidism was confirmed by observing the weight change, thyroid weight change, content change in blood thyroid hormone (TSH, T3, and T4), and histopathological changes in the thyroid (the total thickness of thyroid in which the cells have been cut and average diameter of thyroid follicle) of the rats for each group.

B. Change in Weight

In the case of hypothyroidism, it is generally known that weight gain occurs because metabolism is being delayed, catabolism is decreased, and glycoprotein in tissues is deposited by the insufficient secretion of thyroid hormone. However, in order to compensate the weight gain caused by hypothyroidism, leptin secretion may be increased, and consequently, appetite may be decreased, metabolic rate may be increased, and weight loss may be induced (Korean Endocrinology Journal, 17(2):197-205, 2002). However, since the administration of at least 10 mg/kg PTU is known to induce significant weight loss (Toxicol Sci 69(1):79-91, 2002), generally, significant weight loss is considered to be induced in a PTU-induced hypothyroidism animal model (Life Sci 84(11-12):372-379, 2009).

Figure 6:
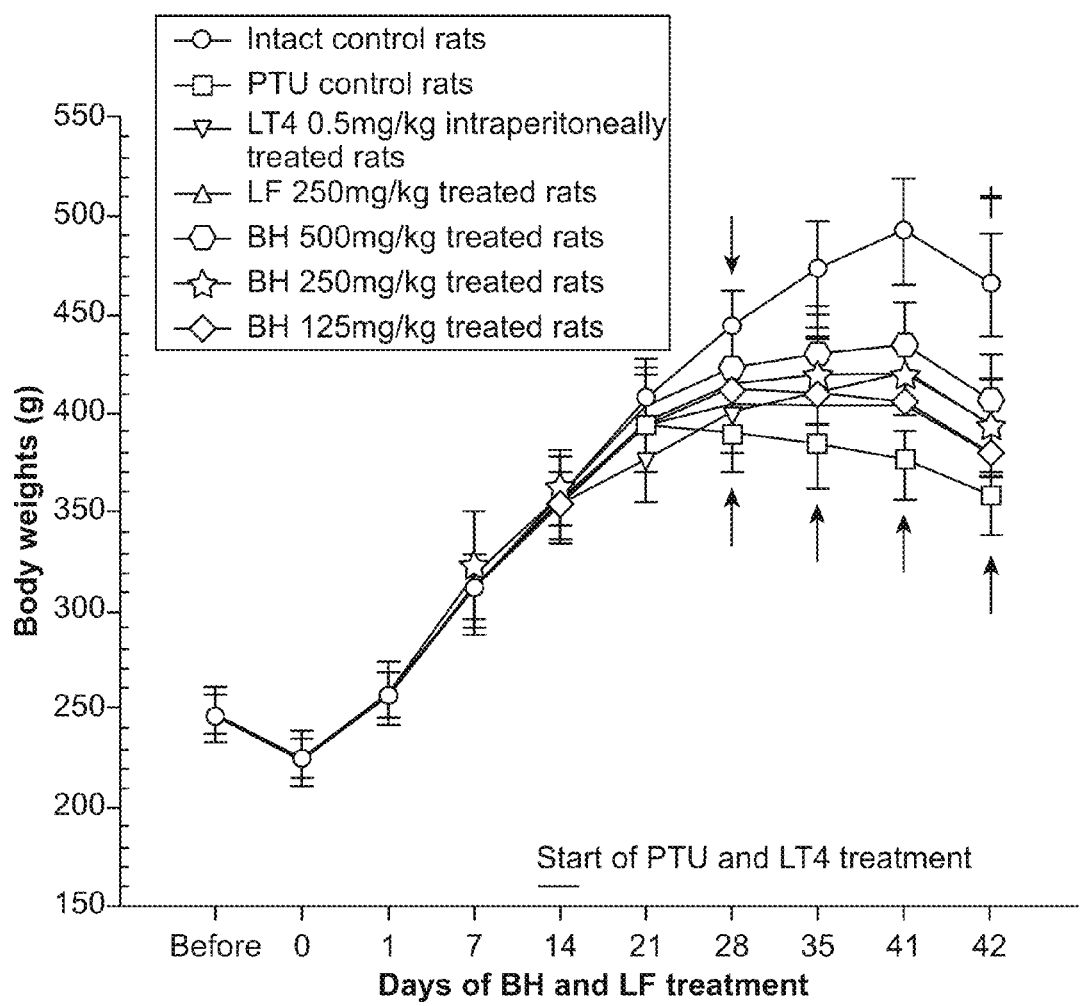
FIG. 6 shows a diagram that shows change in weight for both intact control rat and PTU-induced hypothyroidism rat.
Figure 7:
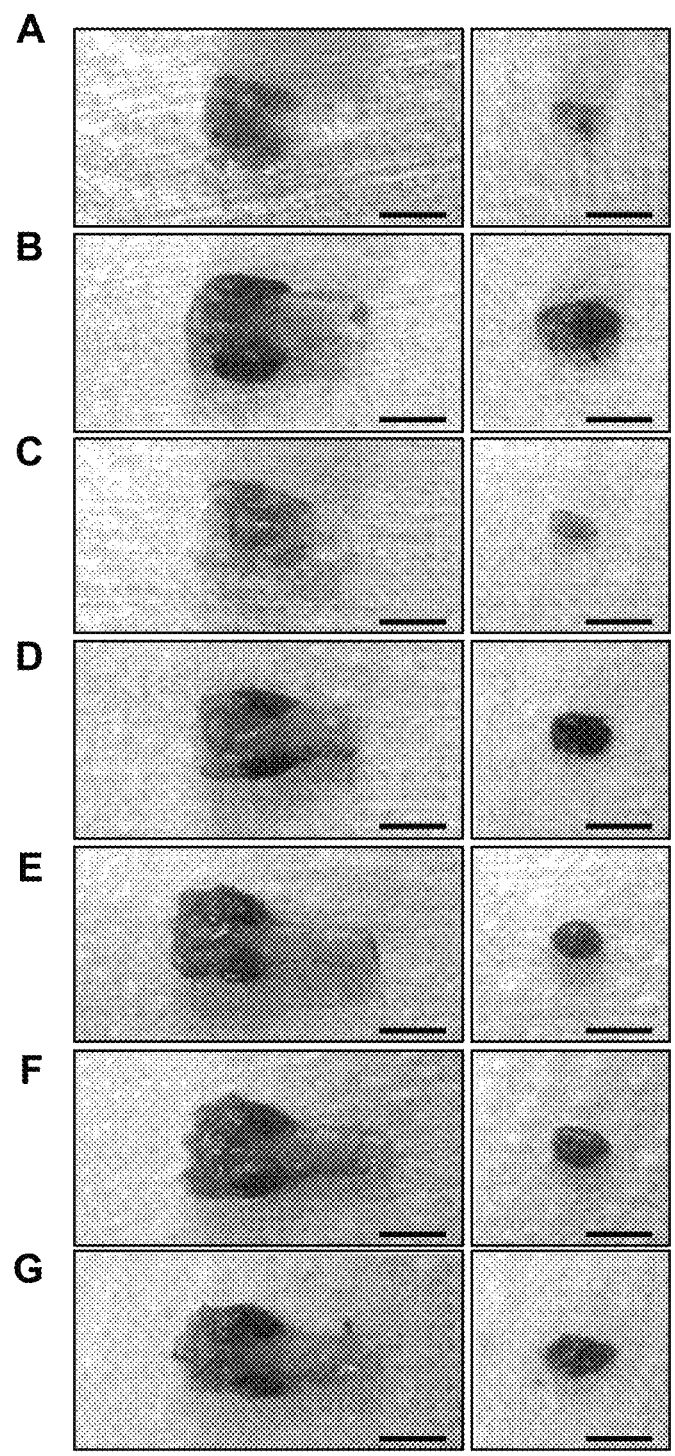
FIG. 7 shows an image of the thyroid extracted from both intact control rat and PTU-induced hypothyroidism rat.
Figure 8:
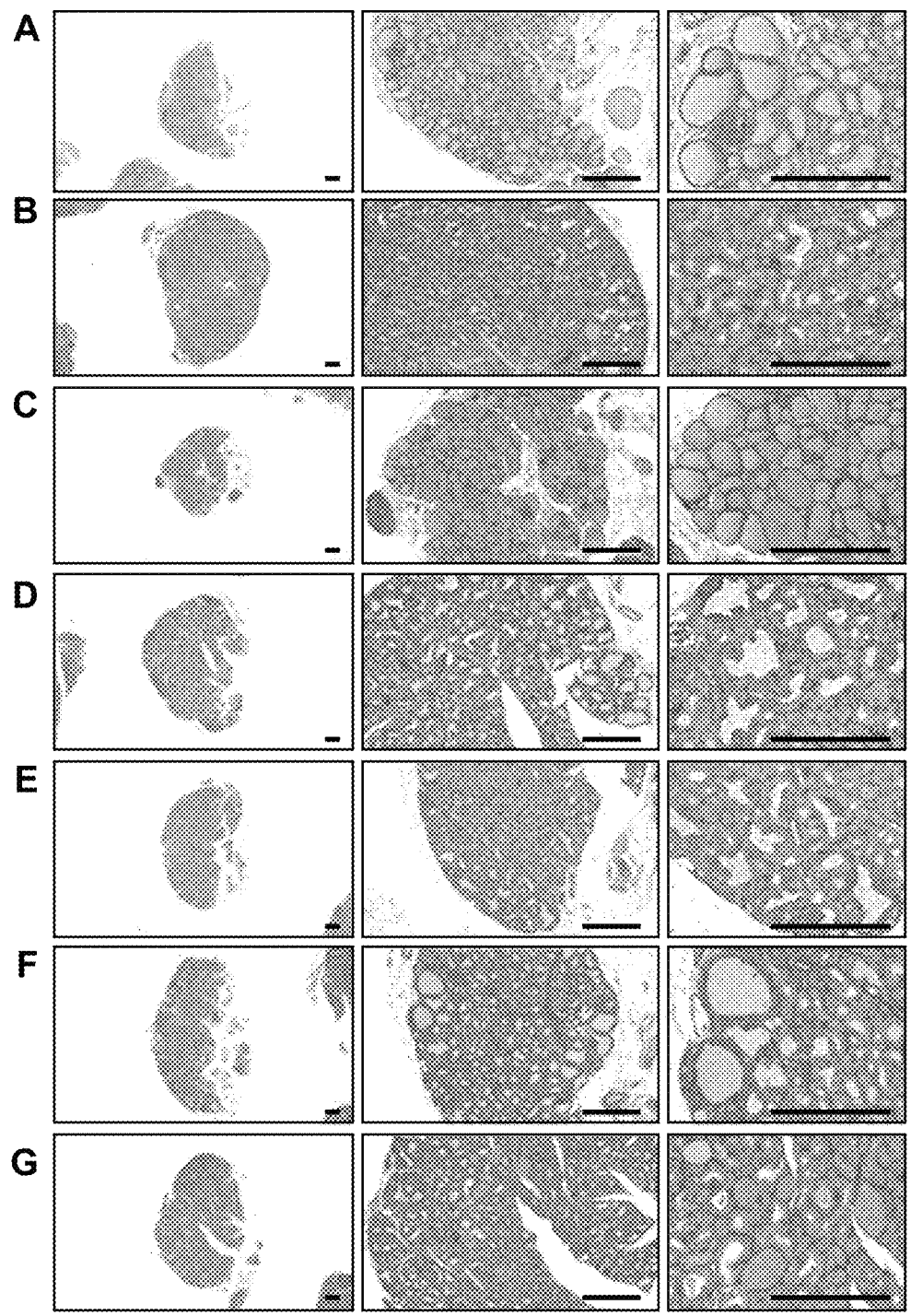
FIG. 8 shows a histopathological image of the thyroid extracted from both intact control rat and PTU-induced hypothyroidism rat.
Figure 9:
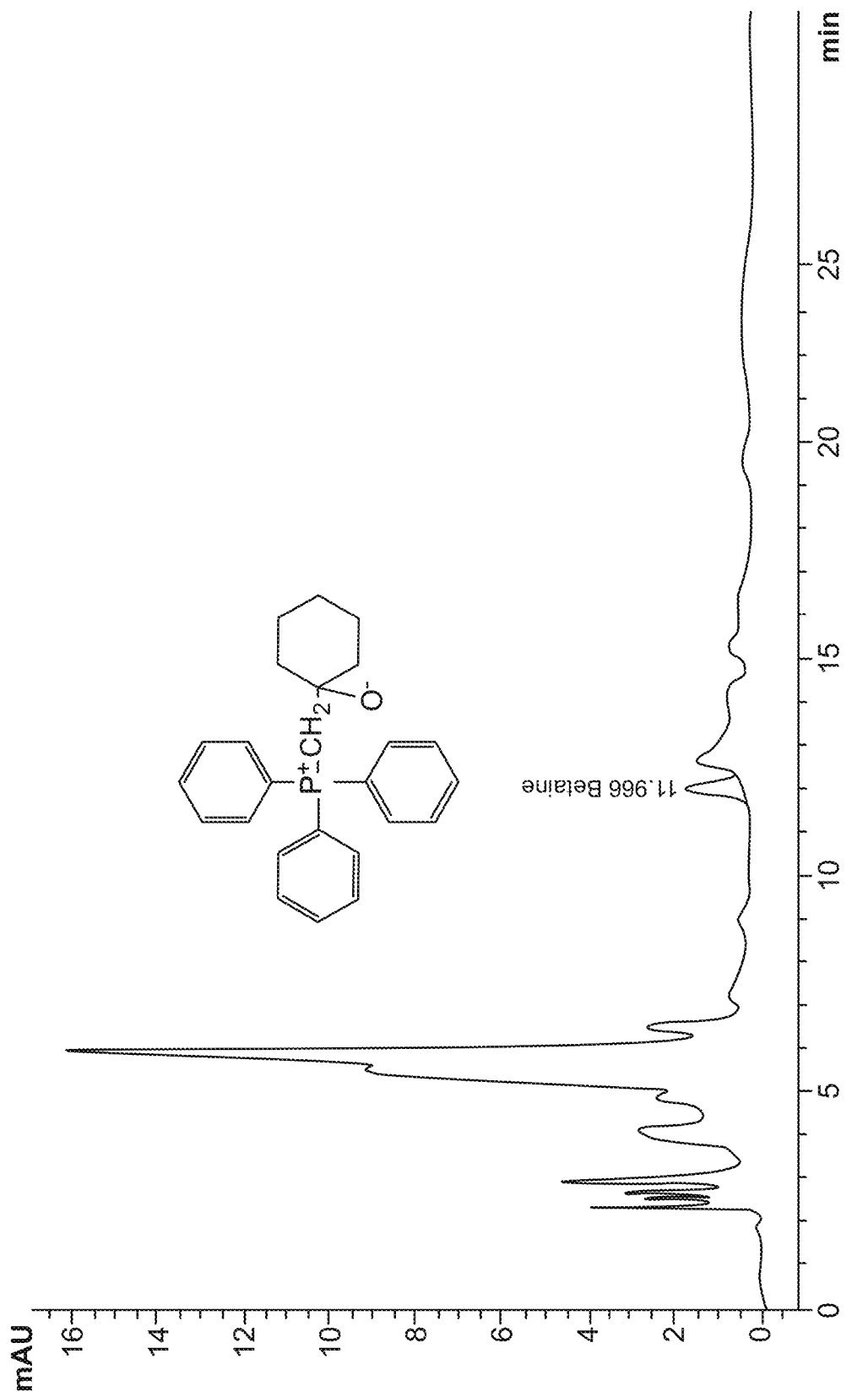
FIG. 9 shows a diagram that shows a HPLC graph of betaine contained in the extract from *Lonicera caerulea L. car. Edulis*.
Figure 10D:
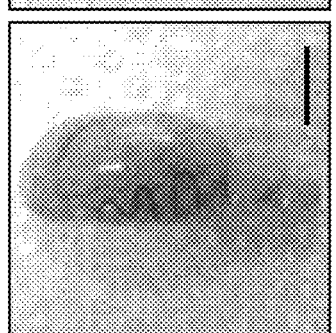
FIG. 10 shows an image of testis and epididymis extracted from both intact control rat and PTU-induced hypothyroidism rat.
Figure 10C:
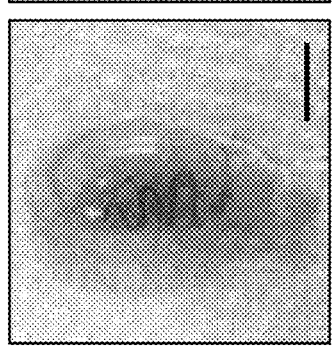
Figure 10G:
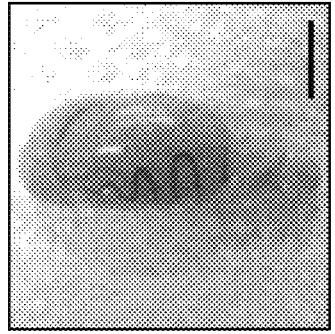
Figure 10B:
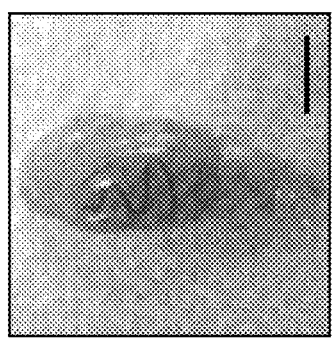
Figure 10F:
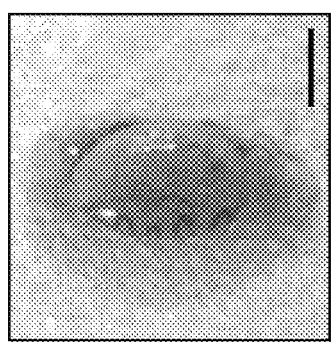
Figure 10A:
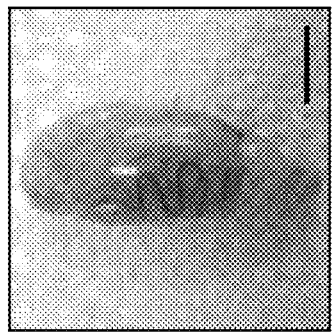
Figure 10E:
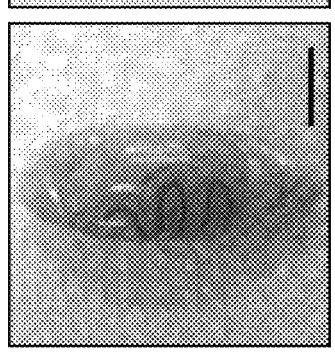
Figure 11:
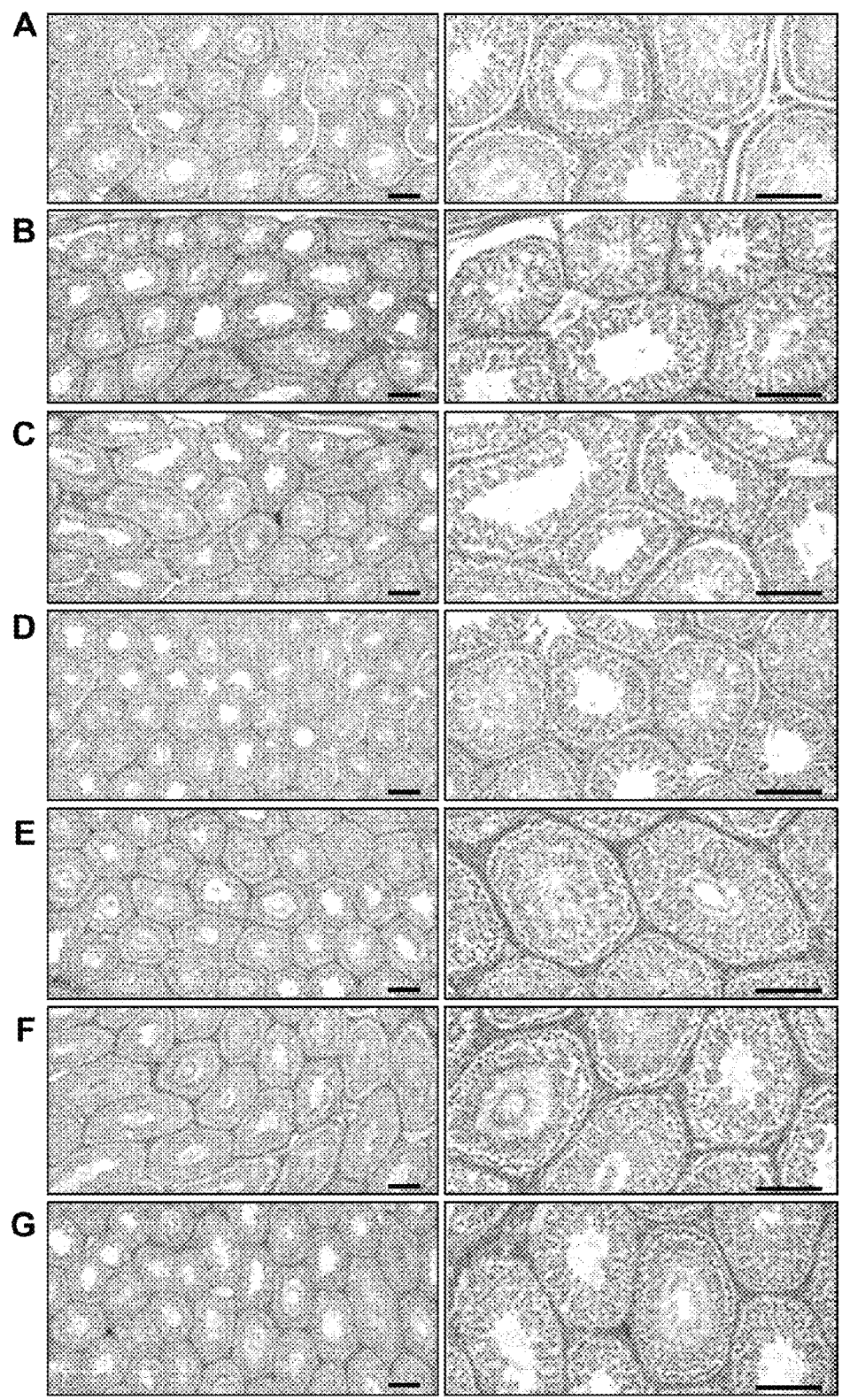
FIG. 11 shows a histopathological image of the testis extracted from intact control rat and PTU-induced hypothyroidism rat.
Figure 12:
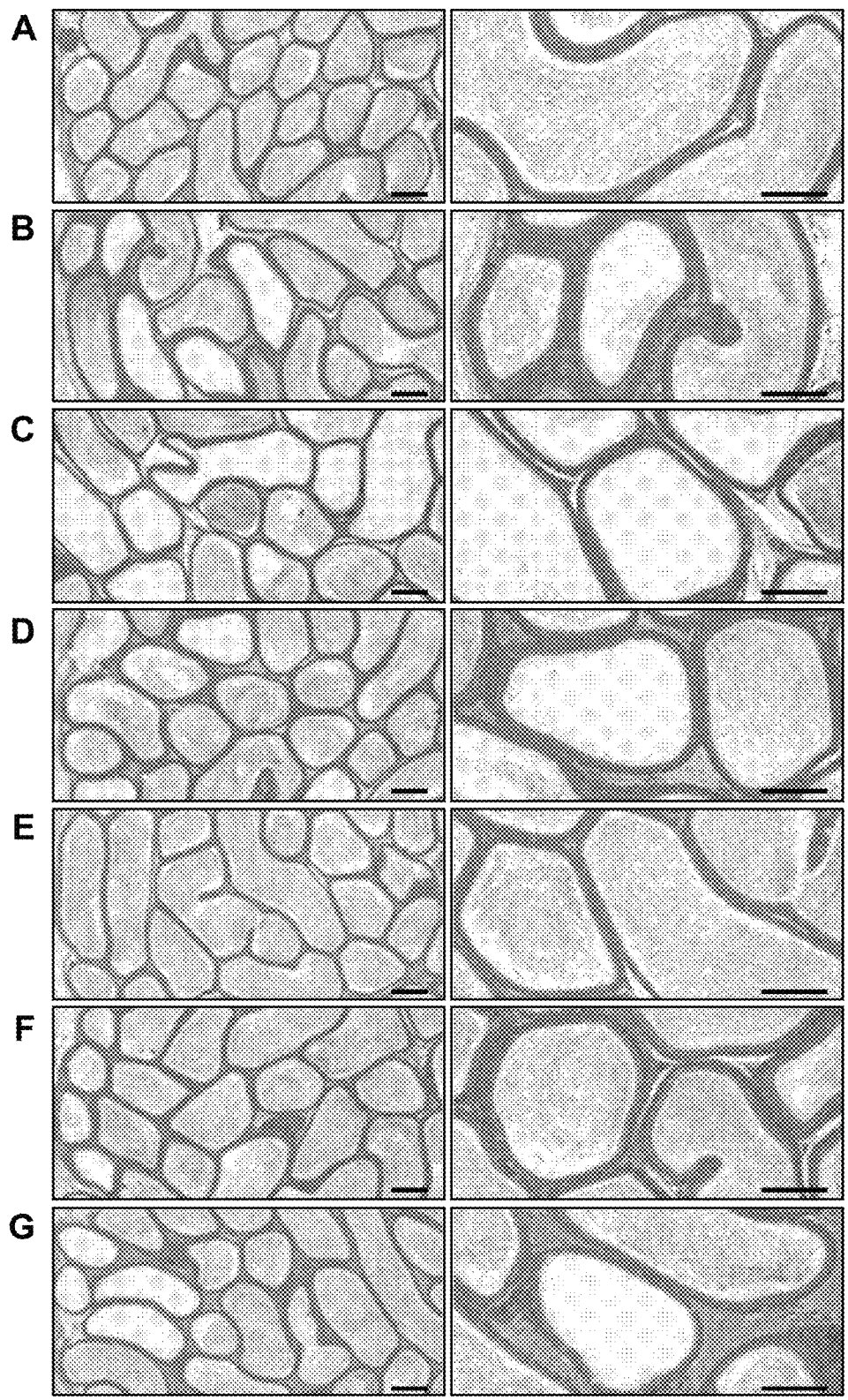
FIG. 12 shows a histopathological image of the epididymis extracted from intact control rat and PTU-induced hypothyroidism rat.
Figure 13:
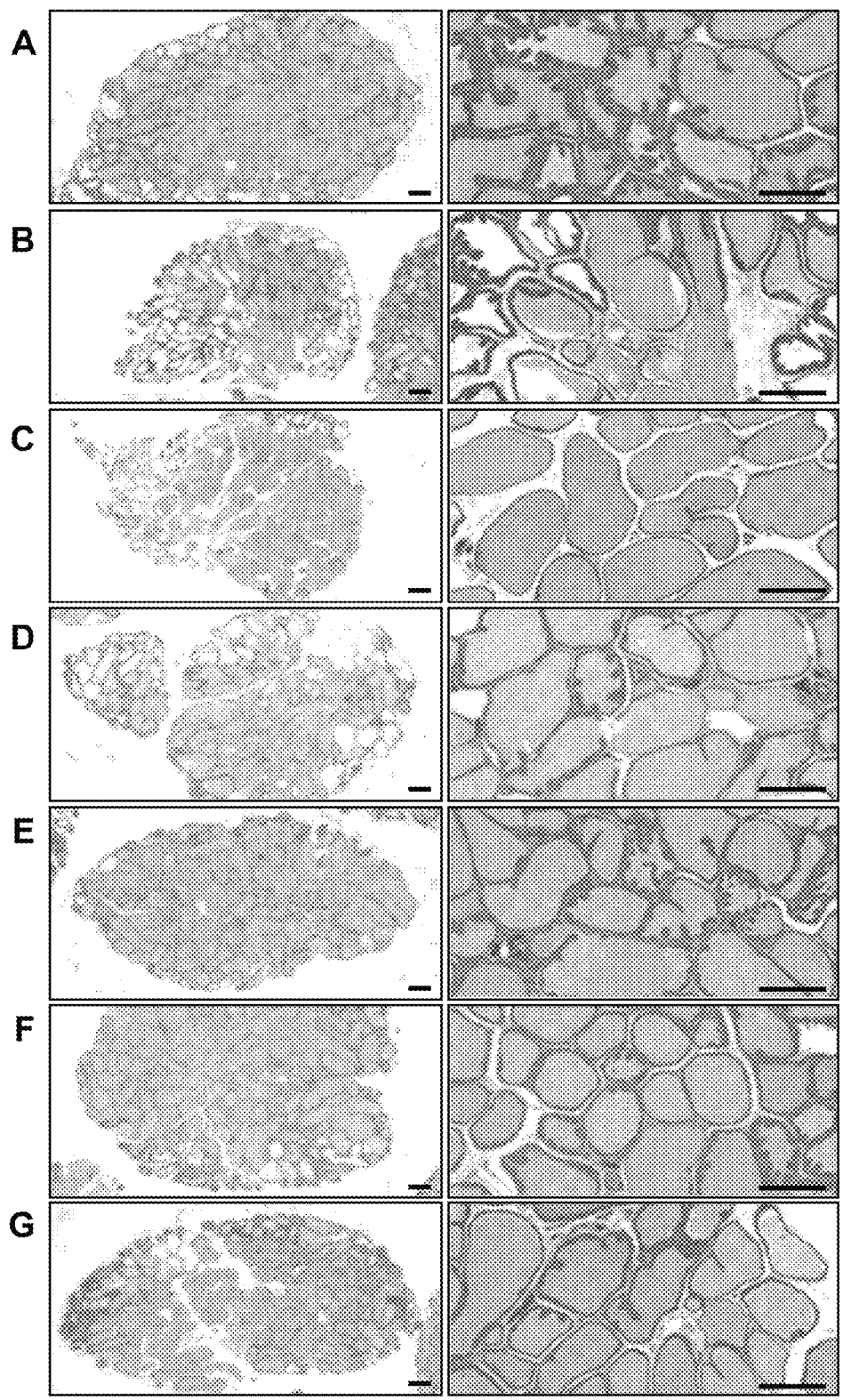
FIG. 13 shows a histopathologic image of the prostate extracted from intact control rat and PTU-induced hypothyroidism rat.

As the result of the experiment, in the PTU control group, a considerable decrease of weight was recognized 2 weeks after PTU administration, and weight gain was also considerably decreased during 4 weeks of PTU administration period and 6 weeks of pre-experimental periods, compared to the intact control group. However, it was confirmed that the decrease of weight and weight gain were considerably inhibited in LF 250 mg/kg, BH (500, 250 and 125 mg/kg) orally administered groups. The results suggest that BH effectively inhibits the weight loss caused by PTU-administered hypothyroidism (Table 7, FIG. 6).

TABLE 7

| | Body weight gains during | | |
|---|---|---|---|
| Groups | 2 weeks of test material pretreatment | 4 weeks of PTU treatment | 6 weeks of total experiments |
| Controls | | | |
| Intact | 133.00 ± 24.14 | 106.00 ± 23.62 | 239.00 ± 25.88 |
| PTU Reference | 129.63 ± 12.51 | 0.75 ± 3.24$^f$ | 130.38 ± 10.20$^a$ |
| LT4 0.5 mg/kg | 127.50 ± 13.15 | 45.50 ± 14.55$^{fg}$ | 173.00 ± 16.75$^{ab}$ |
| LF 250 mg/kg | 131.50 ± 8.90 | 20.13 ± 4.94$^{fg}$ | 151.63 ± 8.55$^{ac}$ |
| BH treated | | | |
| 500 mg/kg | 137.38 ± 11.36 | 44.25 ± 10.89$^{fgh}$ | 181.63 ± 17.12$^{abd}$ |
| 250 mg/kg | 135.88 ± 10.41 | 32.88 ± 10.79$^{fgh}$ | 168.75 ± 16.78$^{abe}$ |
| 125 mg/kg | 134.25 ± 13.26 | 23.75 ± 8.53$^{fg}$ | 158.00 ± 15.44$^{ab}$ |

Values are expressed as Mean ± S.D. of eight rats
PTU = Propylithiouracil, 6-n-Propyl-2-thiouracil
LT4 = Levothyroxine
LF = *Lonicerae* Flos lyophilized aqueous extracts
BH = Blue honeysuckle lyophilized concentrated powder
$^a$p < 0.01 as compared with intact control by LSD test
$^b$p < 0.01 and $^c$p < 0.05 as compared with PTU control by LSD test
$^d$p < 0.01 and $^e$p < 0.05 as compared with LF 250 mg/kg by LSD test
$^f$p < 0.01 as compared with intact control by MW test
$^g$p < 0.01 as compared with PTU control by MW test
$^h$p < 0.01 as compared with LF 250 mg/kg by MW test C. Change in the Thyroid Weight In the PTU administered control group, it was confirmed that thyroid was considerably grown and the absolute and relative weights of thyroid were also considerably increased compared to the intact control group not administered with PTU.

On the other hand, a considerable decrease of absolute and relative thyroid weights was recognized in all the experimental groups including the LT4 administered group and BH treated group, respectively, compared to the PTU control group. Specifically, the decrease of the thyroid weight was considerably large in the BH (500 mg/kg, 250 mg/kg, 125 mg/kg) administered groups compared to the LF (250 mg/kg) administered group (Table 8).

TABLE 8

| Groups | Absolute organ weights (g) Thyroid gland | Relative organ weights (% of body weights) Thyroid gland |
|---|---|---|
| Controls | | |
| Intact | 0.012 ± 0.003 | 0.003 ± 0.001 |
| PTU Reference | 0.035 ± 0.004$^a$ | 0.010 ± 0.001$^a$ |
| LT4 0.5 mg/kg | 0.012 ± 0.003$^c$ | 0.003 ± 0.001$^c$ |
| LF 250 mg/kg | 0.026 ± 0.004$^{ac}$ | 0.007 ± 0.001$^{ac}$ |

TABLE 8-continued

|  | Absolute organ weights (g) Thyroid gland | Relative organ weights (% of body weights) Thyroid gland |
| --- | --- | --- |
| Groups | | |
| BH treated | | |
| 500 mg/kg | 0.018 ± 0.004[bcd] | 0.004 ± 0.001[ace] |
| 250 mg/kg | 0.020 ± 0.005[acd] | 0.005 ± 0.001[ace] |
| 125 mg/kg | 0.024 ± 0.006[ac] | 0.006 ± 0.002[ac] |

Values are expressed as Mean ± S.D. of eight rats
PTU = Propylthiouracil, 6-n-propyl-2-thiouracil
LT4 = Levothyroxine
LF = *Lonicerae* Flos lyophilized aqueous extracts
BH = Blue honeysuckle lyophilized concentrated powder
[a]$p < 0.01$ and [b]$p < 0.05$ as compared with intact control by LSD test
[c]$p < 0.01$ as compared with PTU control by LSD test
[d]$p < 0.01$ as compared with LF 250 mg/kg by LSD test
[e]$p < 0.01$ as compared with intact control by MW test
[f]$p < 0.01$ and [g]$p < 0.05$ as compared with PTU control by MW test
[h]$p < 0.01$ as compared with LF 250 mg/kg by MW test D. Change the Thyroid Hormone Content in Blood The TSH content in blood was considerably increased and the T3 and T4 contents in blood were considerably decreased in the PTU administered control group compared to the intact control group not administered with PTU.

On the other hand, a considerable decrease in the TSH content and a considerable increase in the T3 and T4 contents were confirmed in all the experimental groups including LT4 administered group and BH treated rats, respectively, compared to the PTU control group. Specifically, a considerable decrease in the TSH content and a considerable increase in T3 and T4 contents were confirmed in the BH (500, 250, and 125 mg/kg) administered groups (Table 9).

TABLE 9

|  | Serum thyroid hormone levels | | |
| --- | --- | --- | --- |
| Groups | TSH (ng/ml) | Tri-iodothyronine (ng/ml) | Thyroxine (µg/ml) |
| Controls | | | |
| Intact | 13.61 ± 1.87 | 74.52 ± 10.36 | 5.60 ± 1.18 |
| PTU Reference | 53.37 ± 10.12[a] | 18.42 ± 5.81[a] | 0.81 ± 0.23[a] |
| LT4 0.5 mg/kg | 10.74 ± 1.62[bc] | 19.24 ± 3.21[a] | 6.75 ± 1.45[e] |
| LF 250 mg/kg | 41.42 ± 6.47[ac] | 32.60 ± 7.75[ac] | 1.50 ± 0.31[ac] |
| BH treated | | | |
| 500 mg/kg | 25.57 ± 7.27[ace] | 55.14 ± 11.90[ace] | 2.30 ± 0.47[ace] |
| 250 mg/kg | 29.41 ± 9.21[acf] | 49.26 ± 12.28[ace] | 1.95 ± 0.22[acf] |
| 125 mg/kg | 35.26 ± 12.92[ad] | 36.99 ± 13.95[ac] | 1.69 ± 0.30[ac] |

Values are expressed as Mean ± S.D. of eight rats
PTU = Propylthiouracil, 6-n-propyl-2-thiouracil
LT4 = Levothyroxine
LT = *Lonicerae* Flos lyophilized aqueous extracts
BH = Blue honeysuckle lyophilized concentrated powder
TSH = Thyroid stimulating hormone
[a]$p < 0.01$ and [b]$p < 0.05$ as compared with intact control by MW test
[c]$p < 0.01$ and [d]$p < 0.05$ as compared with PTU control by MW test
[e]$p < 0.01$ and [f]$p < 0.05$ as compared with LF 250 mg/kg by MW test E. Histopathological Observation of Thyroid It was confirmed that the total thickness of thyroid was increased and the average thyroid follicular diameter was considerably decreased in the PTU administered control group compared to the intact control group not administered with PTU. This suggests the growth of the thyroid caused by the decrease of colloid substances in the follicle.

On the other hand, it was confirmed that the total thickness of thyroid was considerably decreased and the average thyroid follicular diameter was considerably increased in all the experimental groups including the LT4 administered group and BH treated rats compared to the PTU control group. Specifically, the effects were even more noticeable in the BH (500, 250, and 125 mg/kg) administered groups compared to the LF 250 mg/kg administered group (Table 10).

TABLE 10

|  | Thyroid gland | |
| --- | --- | --- |
| Groups | Total thickness (µm/central regions) | Mean follicular diameters (µm/follicle) |
| Controls | | |
| Intact | 1338.40 ± 123.68 | 134.86 ± 13.03 |
| PTU Reference | 2482.09 ± 203.63[a] | 43.93 ± 11.13[a] |
| LT4 0.5 mg/kg | 1542.77 ± 137.07[bc] | 102.24 ± 12.47[ac] |
| LF 250 mg/kg | 2150.41 ± 157.83[ac] | 75.34 ± 11.03[ac] |
| BH treated | | |
| 500 mg/kg | 1524.22 ± 168.99[bcd] | 98.00 ± 10.14[acd] |
| 250 mg/kg | 1624.87 ± 122.30[acd] | 92.07 ± 14.88[ace] |
| 125 mg/kg | 2052.86 ± 197.31[ac] | 82.89 ± 16.09[ac] |

Values are expressed as Mean ± S.D. of eight rats
PTU = Propylthiouracil, 6-n-propyl-2-thiouracil
LT4 = Levothyroxine
LF = *Lonicerae* Flos lyophilized aqueous extracts
BH = Blue honeysuckle lyophilized concentrated powder
[a]$p < 0.01$ and [b]$p < 0.05$ as compared with intact control by LSD test
[c]$p < 0.01$ as compared with PTU control by LSD test
[d]$p < 0.01$ and [e]$p < 0.05$ as compared with LF 250 mg/kg by LSD test
[f]$p < 0.01$ as compared with intact control by MW test
[g]$p < 0.01$ as compared with PTU controls of by MW test
[h]$p < 0.01$ as compared LF 250 mg/kg by MW test (3) Evaluation of the Influence on Reproductive Organs by Administration of the Extract from *Lonicera caerulea* L. car. *Edulis* Fruits A. Change in the Weight of Reproductive Organs A considerable atrophy of testis and epididymis and a considerable decrease of relative and absolute weights of testis, epididymis, and prostate were observed in PTU administered control group compared to the intact control group.

On the other hand, a considerable increase of the relative and absolute weights of testis, epididymis, and prostate were recognized in the LF administered group and BH treated group, respectively, compared to PTU control group. In contrast, the relative and absolute weights of testis, epididymis, and prostate were considerably decreased in LT4 administered group compared to the PTU control group (Tables 11 and 12).

TABLE 11

|  | Absolute organ weights (g) | | |
| --- | --- | --- | --- |
| Groups | Testis | Epididymis | Prostate |
| Controls | | | |
| Intact | 1.686 ± 0.053 | 0.762 ± 0.063 | 0.918 ± 0.103 |
| PTU Reference | 1.146 ± 0.043[e] | 0.442 ± 0.045[a] | 0.578 ± 0.053[e] |
| LT4 0.5 mg/kg | 1.082 ± 0.045[eg] | 0.342 ± 0.042[ac] | 0.492 ± 0.042[ef] |
| LF 250 mg/kg | 1.379 ± 0.122[ef] | 0.523 ± 0.041[ac] | 0.668 ± 0.033[ef] |

TABLE 11-continued

| | Absolute organ weights (g) | | |
|---|---|---|---|
| Groups | Testis | Epididymis | Prostate |
| BH treated | | | |
| 500 mg/kg | 1.656 ± 0.087$^{fh}$ | 0.659 ± 0.037$^{acd}$ | 0.822 ± 0.104$^{fh}$ |
| 250 mg/kg | 1.568 ± 0.070$^{efh}$ | 0.631 ± 0.038$^{acd}$ | 0.815 ± 0.107$^{fh}$ |
| 125 mg/kg | 1.469 ± 0.140$^{ef}$ | 0.572 ± 0.072$^{c}$ | 0.723 ± 0.120$^{ef}$ |

Values are expressed as Mean ± S.D. of eight rats
PTU = Propylthiouracil, 6-n-propyl-2-thiouracil
LT4 = Levothyroxine
LF = *Lonicerae* Flos lyophilized aqueous extracts
BH = Blue honeysuckle lyophilized concentrated powder
$^{a}p < 0.01$ and $^{b}p < 0.05$ as compared with intact control by LSD test
$^{c}p < 0.01$ as compared with PTU control by LSD test
$^{d}p < 0.01$ as compared with LF 250 mg/kg by LSD test
$^{e}p < 0.01$ as compared with intact control by MW test
$^{f}p < 0.01$ and $^{g}p < 0.05$ as compared with PTU control by MW test
$^{h}p < 0.01$ as compared with LF 250 mg/kg by MW test

TABLE 12

| | Relative organ weights (% of body weights) | | |
|---|---|---|---|
| Groups | Testis | Epididymis | Prostate |
| Controls | | | |
| Intact | 0.364 ± 0.022 | 0.165 ± 0.019 | 0.198 ± 0.023 |
| PTU Reference | 0.322 ± 0.026$^{a}$ | 0.124 ± 0.013$^{g}$ | 0.162 ± 0.014$^{g}$ |
| LT4 0.5 mg/kg | 0.273 ± 0.021$^{ac}$ | 0.086 ± 0.012$^{gi}$ | 0.124 ± 0.013$^{gf}$ |
| LF 250 mg/kg | 0.365 ± 0.033$^{d}$ | 0.138 ± 0.010$^{gj}$ | 0.177 ± 0.008$^{hj}$ |
| BH treated | | | |
| 500 mg/kg | 0.408 ± 0.025$^{ace}$ | 0.162 ± 0.008$^{ik}$ | 0.202 ± 0.022$^{il}$ |
| 250 mg/kg | 0.399 ± 0.025$^{bcf}$ | 0.161 ± 0.013$^{ik}$ | 0.207 ± 0.027$^{ik}$ |
| 125 mg/kg | 0.387 ± 0.053$^{c}$ | 0.151 ± 0.024$^{j}$ | 0.189 ± 0.029 |

Values are expressed as Mean ± S.D. of eight rats
PTU = Propylthiouracil, 6-n-propyl-2-thiouracil
LT4 = Levothyroxine
LF = *Lonicerae* Flos lyophilized aqueous extracts
BH = Blue honeysuckle lyophilized concentrated powder
$^{a}p < 0.01$ and $^{b}p < 0.05$ as compared with intact control by LSD test
$^{c}p < 0.01$ and $^{d}p < 0.05$ as compared with PTU control by LSD test
$^{e}p < 0.01$ and $^{f}p < 0.05$ as compared with LF 250 mg/kg by LSD test
$^{g}p < 0.01$ and $^{h}p < 0.05$ as compared with intact control by MW test
$^{i}p < 0.01$ and $^{j}p < 0.05$ as compared with PTU control by MW test
$^{k}p < 0.01$ and $^{l}p < 0.05$ as compared with LF 250 mg/kg by MW test B. Change in the Content of Sex Hormones in Serum Considerably increased level of serum follicle stimulating hormone and considerably decreased level of testosterone and dihydrotestosterone (DHT) were observed in PTU administered control group compared to the intact control group.

On the other hand, a considerably decreased level of serum follicle stimulating hormone and considerably increased level of testosterone and DHT were recognized in the LF administered group and BH treated group, respectively, compared to PTU control group. In contrast, the level of serum follicle stimulating hormone was considerably increased and the levels of testosterone and DHT were decreased in LT4 administered group compared to PTU control group (Table 13).

TABLE 13

| | Serum male reproductive hormone levels | | |
|---|---|---|---|
| Groups | Testosterone (ng/ml) | DHT (pg/ml) | FSH (ng/ml) |
| Controls | | | |
| Intact | 3.07 ± 0.42 | 184.25 ± 16.74 | 10.14 ± 2.32 |
| PTU Reference | 1.69 ± 0.16$^{f}$ | 118.75 ± 8.43$^{a}$ | 18.24 ± 2.03$^{a}$ |
| LT4 0.5 mg/kg | 1.45 ± 0.18$^{fi}$ | 98.00 ± 13.43$^{ab}$ | 21.01 ± 1.65$^{ab}$ |
| LF 250 mg/kg | 2.10 ± 0.13$^{fh}$ | 133.38 ± 10.78$^{ac}$ | 15.61 ± 1.03$^{ab}$ |
| BH treated | | | |
| 500 mg/kg | 2.61 ± 0.33$^{ghj}$ | 161.88 ± 11.46$^{abd}$ | 12.46 ± 1.20$^{abd}$ |
| 250 mg/kg | 2.49 ± 0.36$^{ghk}$ | 154.00 ± 13.78$^{abd}$ | 13.71 ± 1.42$^{abe}$ |
| 125 mg/kg | 2.21 ± 0.46$^{gh}$ | 139.63 ± 13.78$^{ab}$ | 14.95 ± 1.93$^{ab}$ |

Values are expressed as Mean ± S.D. of eight rats
PTU = Propylthiouracil, 6-n-propyl-2-thiouracil
LT4 = Levothyroxine
LF = *Lonicerae* Flos lyophilized aqueous extracts
BH = Blue honeysuckle lyophilized concentrated powder|
DHT = Dihydrotestosterone
FSH = Follicular stimulating hormone
$^{a}p < 0.01$ as compared with intact control by LSD test
$^{b}p < 0.01$ and $^{c}p < 0.05$ as compared with PTU control by LSD test
$^{d}p < 0.01$ and $^{e}p < 0.05$ as compared with LF 250 mg/kg by LSD test
$^{f}p < 0.01$ and $^{g}p < 0.05$ as compared wth intact control by MW test
$^{h}p < 0.01$ and $^{i}p < 0.05$ as compared with PTU control by MW test
$^{j}p < 0.01$ and $^{k}p < 0.05$ as compared with LF 250 mg/kg by MW test C. Change in Testicular Antioxidant Defense System Small decrease in lipid peroxidation in testis, considerable increase in the $H_2O_2$ level, and considerable decrease in superoxide dismutase (SOD) and catalase (CAT) activities within testis were observed in PTU administered control group compared to the intact control group.

On the other hand, considerably decreased level of $H_2O_2$ and increased level of SOD and CAT activities within testis were recognized in LF administered group and BH treated group, respectively, compared to PTU control group. In contrast, the $H_2O_2$ level was considerably increased and the SOD and CAT activities were considerably decreased in LT4 administered group compared to PTU control group (Table 14).

TABLE 14

| | Lipid peroxidation | Antioxidant defense system | | |
|---|---|---|---|---|
| Groups | Malondialdehyde (nM/mg protein) | $H_2O_2$ (nM/mg protein) | SOD (U/mg protein) | Catalase (U/mg protein) |
| Controls | | | | |
| Intact | 5.34 ± 0.09 | 23.00 ± 5.24 | 41.88 ± 12.99 | 36.00 ± 10.42 |
| PTU | 4.85 ± 0.97 | 57.88 ± 12.19$^{a}$ | 14.88 ± 2.75$^{e}$ | 13.50 ± 3.02$^{e}$ |

TABLE 14-continued

| Groups | Lipid peroxidation Malondialdehyde (nM/mg protein) | Antioxidant defense system | | |
|---|---|---|---|---|
| | | $H_2O_2$ (nM/mg protein) | SOD (U/mg protein) | Catalase (U/mg protein) |
| Reference | | | | |
| LT4 0.5 mg/kg | 5.54 ± 0.91 | 80.63 ± 16.27$^{ab}$ | 8.50 ± 2.00$^{eg}$ | 8.63 ± 2.13$^{eg}$ |
| LF 250 mg/kg | 4.86 ± 1.12 | 43.13 ± 5.64$^{ab}$ | 21.75 ± 4.65$^{eg}$ | 19.63 ± 2.50$^{eg}$ |
| BH treated | | | | |
| 500 mg/kg | 4.65 ± 0.70 | 26.25 ± 6.73$^{bc}$ | 33.38 ± 9.04$^{gh}$ | 27.75 ± 3.49$^{gh}$ |
| 250 mg/kg | 4.67 ± 0.82 | 32.00 ± 6.85$^{bd}$ | 29.13 ± 4.94$^{gh}$ | 23.75 ± 2.12$^{egh}$ |
| 125 mg/kg | 4.54 ± 1.03 | 38.50 ± 11.82$^{ab}$ | 22.50 ± 5.88$^{eg}$ | 21.88 ± 7.18$^{eg}$ |

Values are expressed as Mean ± S.D. of eight rats
PTU = Propylthiouracil, 6-n-propyl-2-thiouracil
LT4 = Levothyroxine
LF = *Lonicerae* Flos lyophilized aqueous extracts
BH = Blue honeysuckle lyophilized concentrated powder
SOD = Supetoxide dismutase
$^a$p < 0.01 as compared with intact control by LSD test
$^b$p < 0.01 as compared with PTU control by LSD test
$^c$p < 0.01 and $^d$p < 0.05 as compared with LF 250 mg/kg by LSD test
$^e$p < 0.01 and $^f$p < 0.05 as compared with intact control by MW test
$^g$p < 0.01 as compared with PTU control by MW test
$^h$p < 0.01 as compared with LF 250 mg/kg by MW test D. Histopathological Observation of Reproductive Organs In comparison with the intact control group, considerable change was observed in PTU administered control group: (1) decreased average diameter of seminiferous tubules and ratio of seminiferous tubules in stages I and II, (2) decreased average diameter of the epididymal ductal head and increased ratio of epididymal duct; and (3) decreased average thickness of prostate ductal epithelium and increased ratio of prostate duct.

On the other hand, in comparison with PTU control group, significant observation was found in: (1) increased average diameter of seminiferous tubules and ratio of seminiferous tubules in stages I and II, (2) increased average diameter of the epididymal ductal head and decreased ratio of epididymal duct; and (3) increased average thickness of prostate ductal epithelium and decreased ratio of prostate duct in LF administered group and BH treated group, respectively. In contrast, in comparison with PTU administered control group, significant observation was found in: (1) decreased average diameter of seminiferous tubules and ratio of seminiferous tubules in stages I and II, (2) decreased average diameter of the epididymal ductal head and increased ratio of epididymal duct; and (3) decreased average thickness of prostate ductal epithelium and increased ratio of prostate duct was in LT4 administered group (Table 15).

The results suggest that BH is effective for (1) the atrophy of seminiferous tubule, epididymal head, and prostate duct caused by hypothyroidism and (2) inhibiting reduction in number of sperms.

TABLE 15

| | Testis | | Epididymis | | Prostate | |
|---|---|---|---|---|---|---|
| Groups | Mean semniferous tubule diameters (μm/tubules) | Stage I~II semniferous tubule percentages (%/mm²) | Mean tubular diameters (μm/ tubules of head) | A/O tubule percentages (%/mm²) | Mean tubular epithelial thickness (μm/tubules) | Atrophic tubule percentage (%/mm²) |
| Controls | | | | | | |
| Intact | 336.13 ± 47.60 | 71.75 ± 10.66 | 329.16 ± 36.15 | 5.25 ± 3.73 | 50.41 ± 10.71 | 5.88 ± 1.73 |
| PTU | 222.88 ± 17.76$^d$ | 26.75 ± 5.99$^d$ | 248.71 ± 12.00$^d$ | 41.50 ± 6.70$^d$ | 19.06 ± 2.87$^d$ | 58.38 ± 10.65$^a$ |
| Reference | | | | | | |
| LT4 0.5 mg/kg | 195.00 ± 13.29$^{df}$ | 15.63 ± 2.39$^{df}$ | 217.98 ± 14.97$^{df}$ | 56.00 ± 7.52$^{df}$ | 11.82 ± 2.76$^{df}$ | 73.50 ± 10.80$^{ab}$ |
| LF 250 mg/kg | 248.63 ± 15.04$^{dg}$ | 39.98 ± 4.85$^{df}$ | 278.99 ± 16.76$^{df}$ | 32.38 ± 4.84$^{df}$ | 27.23 ± 4.58$^{df}$ | 44.25 ± 7.65$^{ab}$ |

TABLE 15-continued

| | Testis | | Epididymis | | Prostate | |
|---|---|---|---|---|---|---|
| Groups | Mean semniferous tubule diameters (μm/tubules) | Stage I~II semniferous tubule percentages (%/mm$^2$) | Mean tubular diameters (μm/tubules of head) | A/O tubule percentages (%/mm$^2$) | Mean tubular epithelial thickness (μm/tubules) | Atrophic tubule percentage (%/mm$^2$) |
| BH treated | | | | | | |
| 500 mg/kg | 309.38 ± 19.10$^{fh}$ | 56.63 ± 5.07$^{dfh}$ | 318.27 ± 25.44$^{fh}$ | 9.50 ± 2.78$^{efh}$ | 36.61 ± 6.50$^{efh}$ | 21.75 ± 7.36$^{abc}$ |
| 250 mg/kg | 282.13 ± 13.29$^{efh}$ | 51.13 ± 6.10$^{dfh}$ | 305.15 ± 22.98$^{fi}$ | 14.88 ± 3.68$^{dfh}$ | 34.98 ± 5.84$^{dfi}$ | 28.38 ± 3.93$^{abc}$ |
| 125 mg/kg | 254.75 ± 14.59$^{df}$ | 42.00 ± 6.80$^{df}$ | 290.71 ± 27.87$^{df}$ | 28.63 ± 7.21$^{df}$ | 30.37 ± 7.35$^{df}$ | 39.38 ± 7.61$^{ab}$ |

Values are expressed as Mean ± S.D. of eight rats
PTU = Propylthiouracil, 6-n-propyl-2-thiouracil
LT4 = Levothyroxine
LF = *Lonicerae* Flos lyophilized aqueous extracts
BH = Blue honeysuckle lyophilized concentrated powder
A/O = A/oligospermatogonia
$^a$p < 0.01 as compared with intact control by LSD test
$^b$p < 0.01 as compared with PTU control by LSD test
$^c$p < 0.01 as compared with LF 250 mg/kg by LSD test
$^d$p < 0.01 and
$^e$p < 0.05 as compared with intact control by MW test
$^f$p < 0.01 and
$^g$p < 0.05 as compared with PTU control by MW test
$^h$p < 0.01 and
$^i$p < 0.05 as compared with LF 250 mg/kg by MW test

EXPERIMENTAL EXAMPLE 5

Measurement of Betaine Content in the Extract from *Lonicera caerulea L. car. Edulis* Fruits Test liquid for quantification was homogenously mixed with the extract from *Lonicera caerulea L. car. Edulis* fruits. 1 g of the mixture was added to 50 ml of water, subjected to ultrasonic extraction for 1 hour, and was filtered with a membrane filter with a pore size of 0.45 μm or less.

HPLC was conducted utilizing Agilent's 1100 series (Agilent Technologies, Santa Clara, Calif., USA), Agilent G1315B DAD detector, and YMC-Pack Polyamine II (Shimadzu Corp., Tokyo, Japan; 4.6×250 mm, 5 μm). Temperature of the column was analyzed at room temperature, the wavelength of UVD was 210 nm, and the mixture (85:15) of acetonitrile (Sigma-Aldrich, St. Louise, Mo., USA) and water was used as a mobile phase. 10 μl of sample was injected at a flow rate of 1.0 ml/min, and qualification was conducted based on retention time. The sample was quantified 3 repeated times utilizing peak-area method. On the other hand, after preparing the standard undiluted solution, which contained 1 μg of betaine per 1 ml, the diluted solution was designated as a standard solution.

Figure 4:
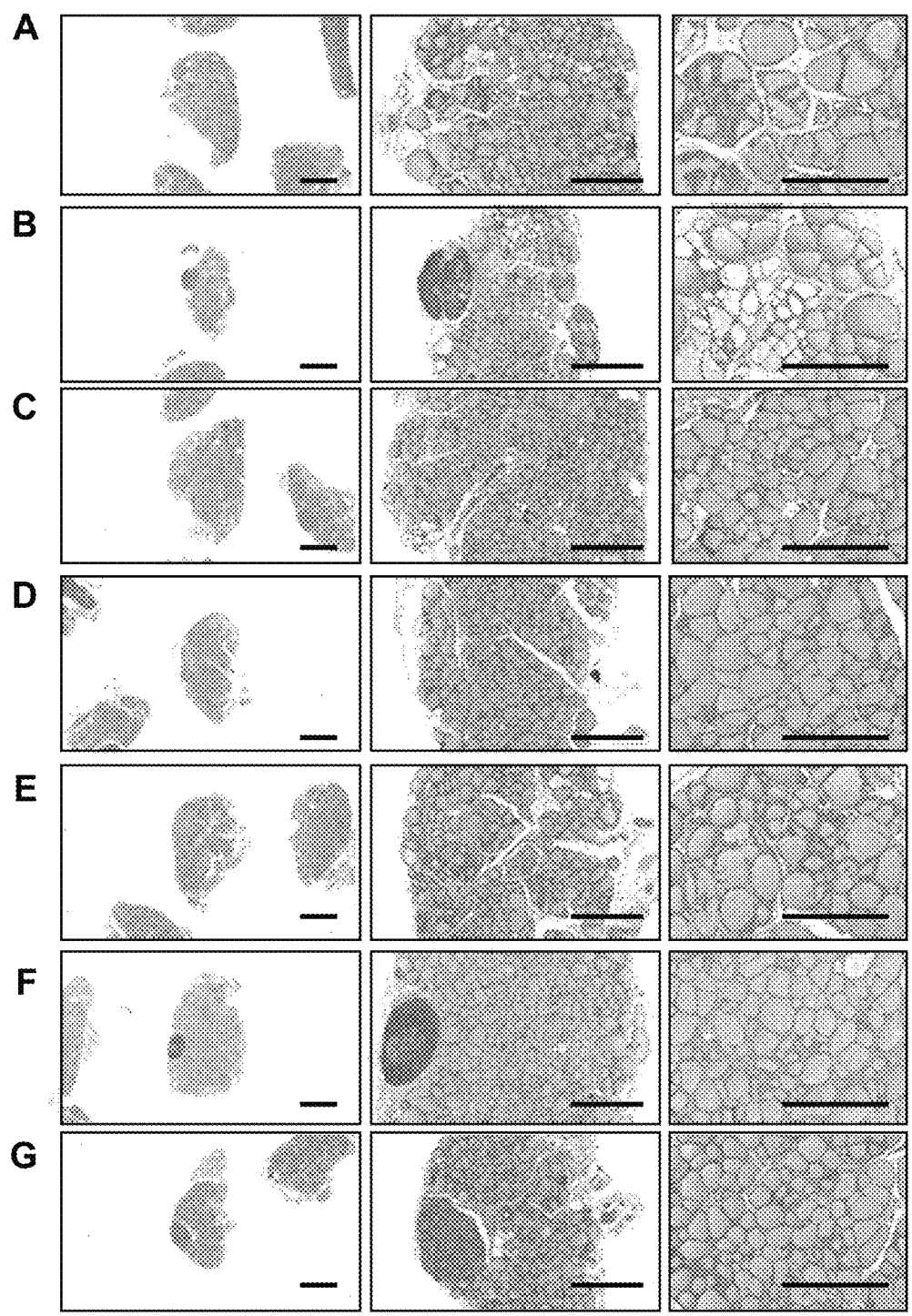
FIG. 4 shows a histopathological image of thyroid extracted from both intact control rat and LT4-induced hyperthyroidism rat.

As the result of measuring the betaine content in BH utilizing HPLC system, the average content of 4.54% (4.45% to 4.63%) was observed (FIG. 4).

PREPARATION EXAMPLE 1

Preparation of Powder Capsules 100 mg of the hot water extract prepared in Example 1 was mixed with 14.8 mg of lactose, 3 mg of crystalline cellulose, and 0.2 mg of magnesium stearate. The mixture was filled into a No. 5 gelatin capsule utilizing a suitable device.

The compositions of powder capsules were as below:
Active ingredient: 100 mg
Lactose: 14.8 mg
crystalline cellulose: 3 mg
Magnesium stearate: 0.2 mg

PREPARATION EXAMPLE 2

Preparation of Injection Fluid

An injection fluid containing 100 mg of the hot water extract prepared in Example 1 was prepared as follows. 100 mg of the hot water extract prepared in Example 1, 600 mg of sodium chloride, and 100 mg of ascorbic acid were dissolved in distilled water, and the final volume was adjusted to 100 ml. This solution was placed in a bottle and heated and sterilized at 120° C. for 30 minutes.

The compositions of the injection fluid were as below:
Active ingredient: 1000 mg
Sodium chloride: 6000 mg
Ascorbic acid: 1000 mg
Distilled water: adequate amount

PREPARATION EXAMPLE 3

Preparation of Powders

Powders were prepared with the following composition based on the method for preparing powder disclosed in the Korean Pharmacopoeia General Medication Provisions.
1) Each sachet contained:
Extract from active ingredient (dried powder): 100 mg
Lactose: 100 mg
Talc: 10 mg
2) Each sachet contained:
Water-soluble fraction of active ingredient: 100 mg
Lactose: 100 mg
Talc: 10 mg

PREPARATION EXAMPLE 4

Preparation of Tablets

Tablets were prepared with the following composition based on the method for preparing tablets disclosed in the Korean Pharmacopoeia General Medication Provisions.

1) Each tablet contained:
Extract from active ingredient (dried powder): 100 mg
Corn starch: 100 mg
Lactose: 100 mg
Magnesium stearate: 2 mg
2) Each tablet contained:
Water-soluble fraction of active ingredient: 100 mg
Corn starch: 100 mg
Lactose: 100 mg
Magnesium stearate: 2 mg

PREPARATION EXAMPLE 5

Preparation of Capsules

Capsules were prepared with the following composition based on the method for preparing capsules disclosed in the Korean Pharmacopoeia General Medication Provisions.
1) Each capsule contained:
Extract from active ingredient (dried powder): 100 mg
Corn starch: 100 mg
Lactose: 100 mg
Magnesium stearate: 2 mg
2) Each capsule contained:
Water-soluble fraction of active ingredient: 100 mg
Corn starch: 100 mg
Lactose: 100 mg
Magnesium stearate: 2 mg

PREPARATION EXAMPLE 6

Preparation of Injection Fluid

Injection fluid was prepared with the following composition based on the method for preparing injection fluid disclosed in the Korean Pharmacopoeia General Medication Provisions.
1) Each ample (2 ml) contained:
Extract from active ingredient (dried powder): 50 mg
Sterile distilled water for injection: adequate amount
pH regulator: adequate amount
2) Each ample (2 ml) contained:
Water-soluble fraction of active ingredient: 50 mg
Sterile distilled water for injection: adequate amount
pH regulator: adequate amount

PREPARATION EXAMPLE 7

Preparation of Solutions

Solutions were prepared with the following composition based on the method for preparing solutions disclosed in the Korean Pharmacopoeia General Medication Provisions.

1) Each solution (100 ml) contained:
Extract of active ingredient (dried powder): 1 mg
Isomerose: 10 g
Mannitol: 5 g
Purified water: adequate amount
2) Each solution (100 ml) contained:
Water-soluble fraction of active ingredient: 100 mg
Isomerose: 10 g
Mannitol: 5 g
Purified water: adequate amount The exemplary embodiments disclosed herein are only for illustrative purposes and should not be construed as limiting the scope of the present invention. On the contrary, the present invention is intended to cover not only the exemplary embodiments but also various alternatives, modifications, equivalents and other embodiments that may be included within the spirit and scope of the present invention as defined by the appended claims.

The invention claimed is:

1. A method for treating thyroid diseases, comprising administering a pharmaceutical composition to a subject in need thereof, wherein the composition comprises an extract from *Lonicera caerulea L. car. Edulis* fruits as an active ingredient.

2. The method according to claim 1, wherein the extract from *Lonicera caerulea L. car. Edulis* fruits is prepared by extracting the extract from *Lonicera caerulea L. car. Edulis* fruits using water, organic solvents, or a mixture thereof.

3. The method according to claim 1, wherein the thyroid diseases are hypothyroidism, hyperthyroidism, thyroid nodule, or thyroiditis.

4. The method according to claim 1, wherein the composition is formulated into any one of forms selected from the group consisting of tablets, pills, powders, granules, capsules, suspension, liquid medicine, emulsion, syrup, sterilized aqueous solution, non-aqueous solution, lyophilized product, and suppository.

5. The method according to claim 1, wherein the composition inhibits damage in reproductive organs caused by thyroid function defects.

6. A method for improving thyroid function, comprising administering a food composition to a subject in need thereof, wherein the composition comprises an extract from *Lonicera caerulea L. car. Edulis* fruits as an active ingredient.

7. The method according to claim 6, wherein the extract from *Lonicera caerulea L. car. Edulis* fruits is prepared by extracting the extract from *Lonicera caerulea L. car. Edulis* fruits using water, organic solvents, or a mixture thereof.

8. The method according to claim 6, wherein the composition inhibits damage in reproductive organs caused by thyroid function defects.

* * * * *

UNITED STATES PATENT AND TRADEMARK OFFICE
CERTIFICATE OF CORRECTION

PATENT NO.        : 9,498,506 B2                              Page 1 of 1
APPLICATION NO.   : 15/023955
DATED             : November 22, 2016
INVENTOR(S)       : Joo Hwan Eom It is certified that error appears in the above-identified patent and that said Letters Patent is hereby corrected as shown below:

In the Claims

Column 30, Line 23, the words "L. car. Edulis" should be changed to "L. var. Edulis."

Column 30, Line 26, the words "L. car. Edulis" should be changed to "L. var. Edulis."

Column 30, Line 27, the words "L. car. Edulis" should be changed to "L. var. Edulis."

Column 30, Line 31, the word "thyroditis" should be changed to "thyroiditis."

Column 30, Line 44, the words "L. car. Edulis" should be changed to "L. var. Edulis."

Column 30, Line 47, the words "L. car. Edulis" should be changed to "L. var. Edulis."

Column 30, Line 48, the words "L. car. Edulis" should be changed to "L. var. Edulis."

Signed and Sealed this
Eleventh Day of April, 2017

Michelle K. Lee
*Director of the United States Patent and Trademark Office*